US010596392B2

(12) United States Patent
Fishman

(10) Patent No.: US 10,596,392 B2
(45) Date of Patent: *Mar. 24, 2020

(54) DERMATOLOGY RADIOTHERAPY SYSTEM WITH HYBRID IMAGER

(71) Applicant: Sensus Healthcare, Inc., Boca Raton, FL (US)

(72) Inventor: Kalman Fishman, Boca Raton, FL (US)

(73) Assignee: SENSUS HEALTHCARE, INC., Boca Raton, FL (US)

(*) Notice: Subject to any disclaimer, the term of this patent is extended or adjusted under 35 U.S.C. 154(b) by 470 days.

This patent is subject to a terminal disclaimer.

(21) Appl. No.: 15/488,071

(22) Filed: Apr. 14, 2017

(65) Prior Publication Data

US 2017/0326385 A1    Nov. 16, 2017

Related U.S. Application Data

(60) Provisional application No. 62/334,839, filed on May 11, 2016.

(51) Int. Cl.
*A61N 5/10* (2006.01)
*A61B 8/08* (2006.01)

(52) U.S. Cl.
CPC .......... *A61N 5/1039* (2013.01); *A61B 8/0858* (2013.01); *A61N 5/1071* (2013.01); *A61N 5/1077* (2013.01); *A61N 2005/1094* (2013.01); *A61N 2005/1096* (2013.01)

(58) Field of Classification Search
CPC .. A61N 5/1039; A61N 5/1071; A61N 5/1077; A61B 8/0858

USPC .................................................... 378/63, 65
See application file for complete search history.

(56) References Cited

U.S. PATENT DOCUMENTS

| 5,892,238 A | 4/1999 | Huttner et al. |
| 2005/0065421 A1 | 3/2005 | Burckhardt |
| 2011/0137177 A1* | 6/2011 | Toma ............... A61B 5/0059 600/473 |
| 2015/0159994 A1 | 6/2015 | Hofmann et al. |
| 2016/0004820 A1 | 1/2016 | Moore |

(Continued)

FOREIGN PATENT DOCUMENTS

| WO | 2013106794 A2 | 7/2013 |
| WO | 2016064750 A1 | 4/2016 |

OTHER PUBLICATIONS

International Search Report and Written Opinion dated Sep. 25, 2017 for PCT/US2017/027715.

(Continued)

*Primary Examiner* — Courtney D Thomas
(74) *Attorney, Agent, or Firm* — Fox Rothschild LLP

(57) ABSTRACT

A radiotherapy system including a radiotherapy component, a structural imaging component, a functional imaging component, and a workstation coupled to the radiotherapy component, the structural imaging component, and the functional imaging component. The workstation includes a processor which combines the structural imaging data and the functional imaging data to produce a fused model for a least a portion of the region of interest, to generate a plan for radiotherapy treatment of the region of interest based on the fused model, and apply, via the radiotherapy component, the radiotherapy treatment.

19 Claims, 10 Drawing Sheets

(56) References Cited

U.S. PATENT DOCUMENTS

2016/0104312 A1  4/2016  Zino et al.
2018/0294052 A1* 10/2018 Fishman ............... G16H 20/40

OTHER PUBLICATIONS

International Search Report dated Jun. 28, 2018 in PCT/US2018/026304.

* cited by examiner

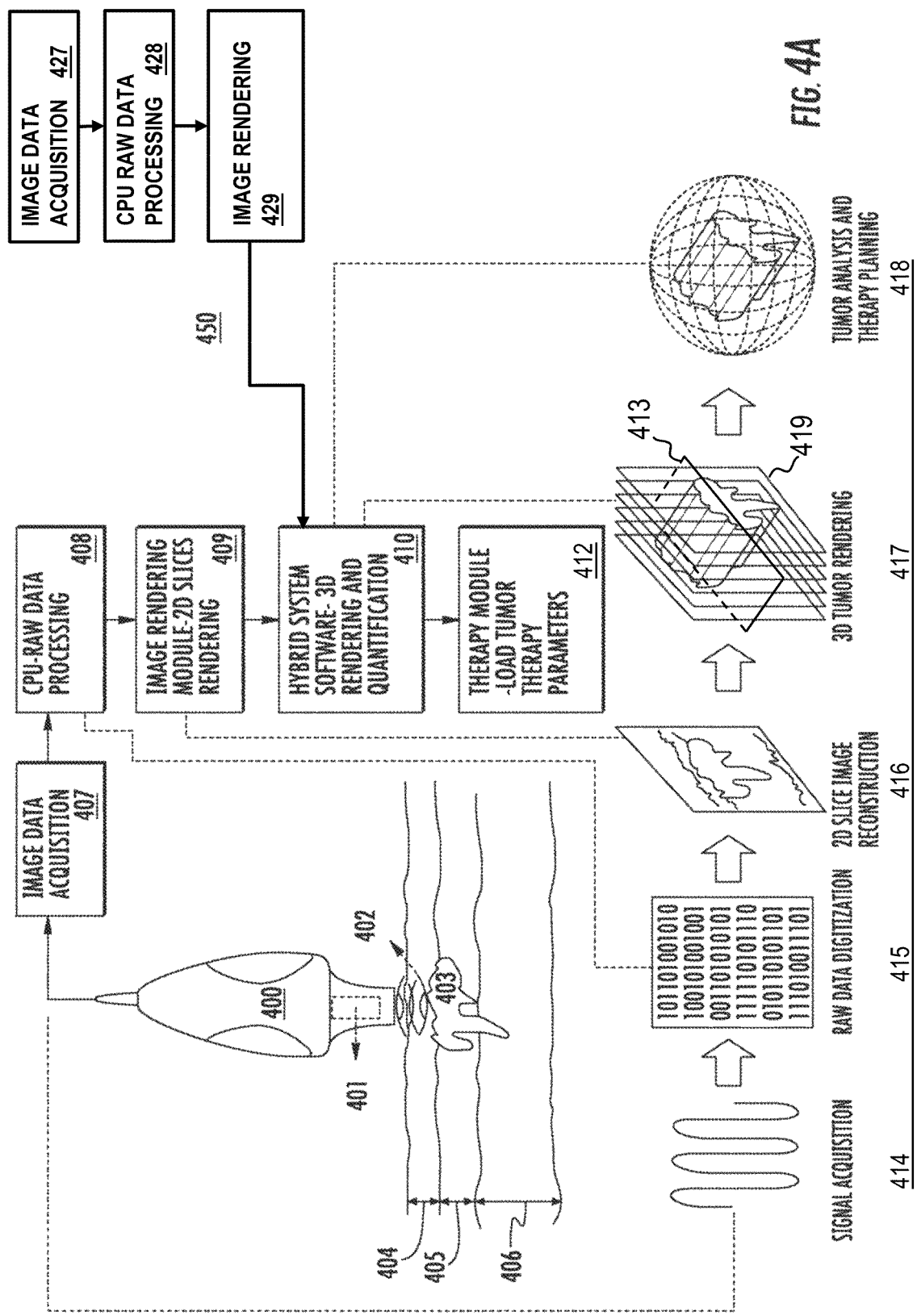

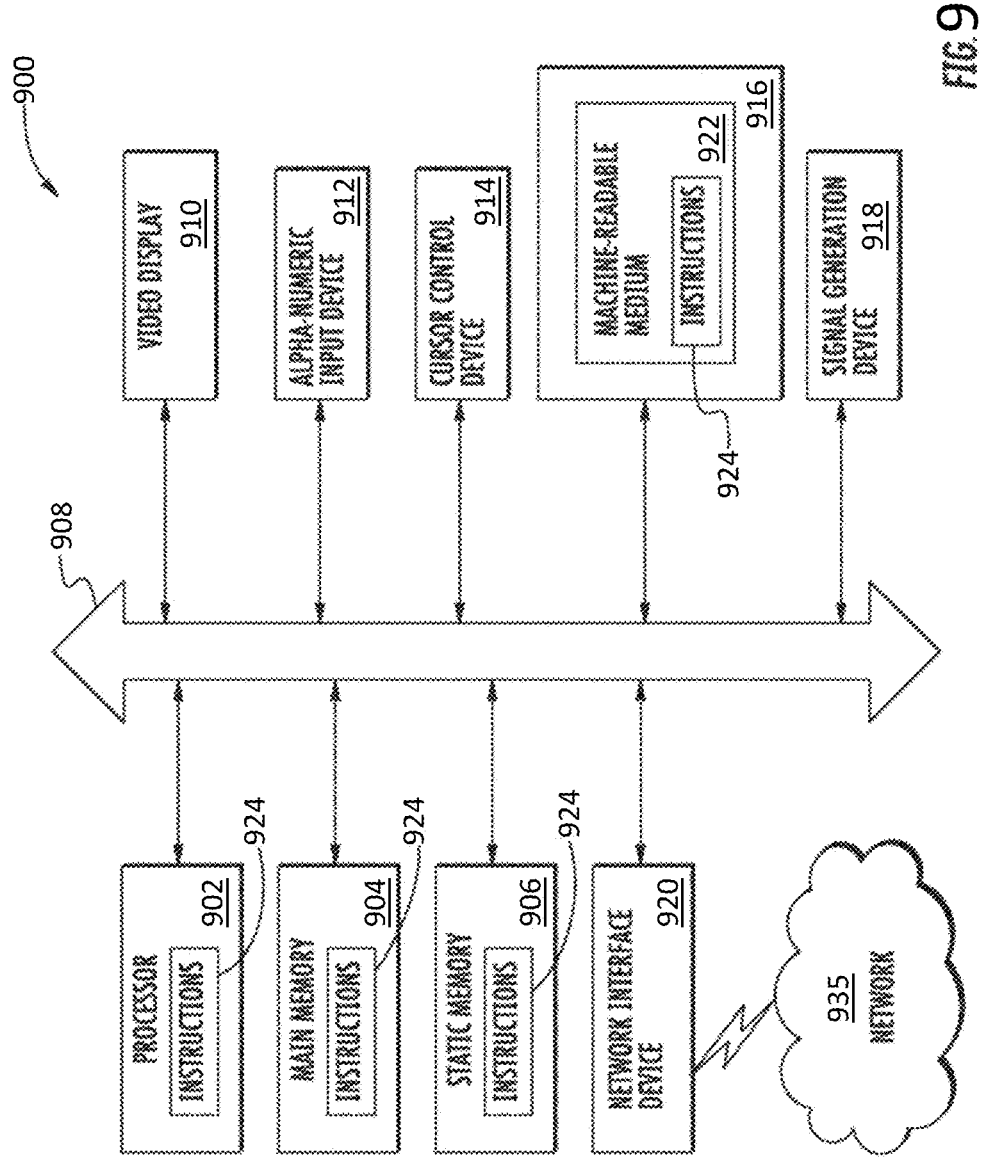

# DERMATOLOGY RADIOTHERAPY SYSTEM WITH HYBRID IMAGER

CROSS-REFERENCE TO RELATED APPLICATION

The present application claims benefit of U.S. Patent Application Ser. No. 62/334,839 filed on May 11, 2016, which application is incorporated herein by reference in its entirety.

FIELD OF THE INVENTION

The disclosure relates to systems, devices and methods for detecting and treating skin conditions such as skin cancers; more particularly it relates to detection of skin cancers and superficial radiotherapy treatment thereof.

BACKGROUND

In the field of radiation oncology accurate imaging is an important component of treating cancer. Images which combine imaging information acquired using different imaging technologies are sometimes referred to as hybrid images. For, example positron emission tomography (PET) is used to image many common types of cancers. Imaging data from PET scanning can be used in combination with other types of imaging data to help treatment specialists more fully understand details of a malignancy. For example image data from PET scanning can be combined with X-ray computed tomography (CT) type scanning.

Once the nature of a cancer is understood by using the appropriate imaging methods, a radiation treatment plan can be determined by a medical practitioner. The treatment plan is usually based on the mass of the tumor, the location, angles of attack which may be used for radiation therapy, how much radiation energy should be applied and so on. There is existing radiation therapy planning (RTP) equipment for this purpose which is made by various manufacturers.

Skin cancer is a type of cancer in which an abnormal growth of cells appears in the skin, and is the most commonly diagnosed type of cancer. The three most common malignant skin cancers are basal cell cancer, squamous cell cancer, and melanoma, each of which is named after the type of skin cell from which it arises. The chances of surviving skin cancer increase if it is detected early and treated appropriately.

For the most part skin cancer is viewed as a simpler problem than other types of cancer. Since it often appears directly on the surface of the skin it is thought of as more of a two-dimensional problem as opposed to a three-dimensional problem as in other types of cancer. So unlike other types of cancers, skin cancers are frequently treated without the use of advanced imaging equipment. Practitioners frequently begin evaluating skin cancers by directly observing the lesion on the surface of the skin, and making an evaluation of what type of cancer might be present based on the appearance of the lesion. The practitioner may then perform a biopsy of the lesion. When the results of the biopsy are obtained at some later date, the practitioner may estimate a margin and depth of skin that must be excised to remove the lesion by surgical or other means. All this is done basically on a visual basis. In other words, there is no true treatment planning facility equivalent to what is done in the radiology field. Unfortunately, this approach to cutaneous oncology can lead to errors with regard to optimal treatment. This suboptimal treatment is in part due to the fact that skin cancer is not approached and quantified like other cancers—even though it is the most prevalent.

SUMMARY OF THE INVENTION

Embodiments of the invention concern the use of novel combinations of hybrid imaging to facilitate treatment of lesions in the field of cutaneous oncology. The hybrid imaging methods described herein are specific to cutaneous oncology and will have various nuances specific to radiation therapy planning ("RTP") oncology for skin cancer. Combined imaging methodologies provide a combination of anatomical and functional/metabolic data. The combined data offer the medical practitioner a highly accurate understanding of the skin cancer problem at hand. This capability is facilitated in a cutaneous oncology work station that uses a unique combination of different imaging modalities and combines the data from each imaging method to facilitate optimal treatment planning.

BRIEF DESCRIPTION OF THE DRAWINGS

FIG. 4A is a flow diagram of a tumor imaging and quantification process.

FIG. 9 is a diagrammatic representation of a machine in the form of a computer system within which a set of instructions, when executed, may cause the machine to perform any one or more of the methodologies discussed herein.

DETAILED DESCRIPTION

Figure 1:
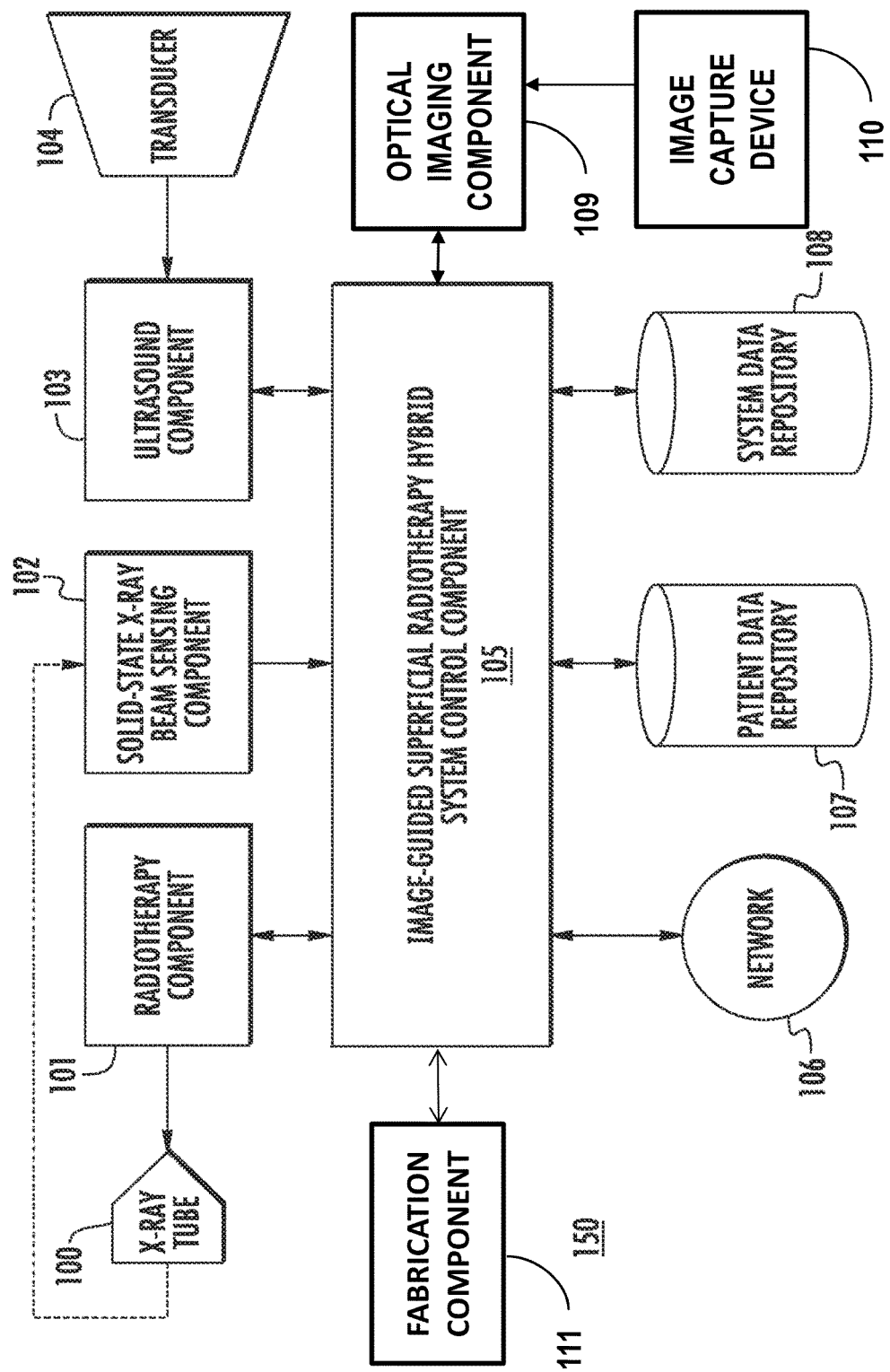
FIG. 1 is a schematic of a high level overview of the components of the system and used in the methods described herein.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

This disclosure relates to systems, devices and methods for detecting and treating skin conditions such as skin cancers; more particularly it relates to detection of skin cancers and superficial radiotherapy treatment thereof. In particular, the present disclosure is directed to a system for dermatological radiotherapy system with a hybrid imager.

A hybrid imaging methodology disclosed herein includes a first imaging methodology that is optimal for imaging structural/anatomical features associated with a particular cutaneous lesion or malignancy, and a second imaging methodology that is optimal for obtaining functional or metabolic features associated with the cutaneous lesion. The imaging modalities are registered and fused to form a hybrid image that combines the best features of both the first and second imaging methodology.

According to one aspect, the first imaging methodology which is used is high frequency ultrasound ("HFU"). HFU is used to give the anatomical imaging modality for viewing very fine and thin tissue. The HFU imaging involves the acquisition of imaging data in a series of two-dimensional (2-D) slices which extend from the outer surface of the skin tissue toward one or more subcutaneous skin layers. A plurality of slices obtained in this way can be combined to render a three-dimensional (3-D) model of the imaged tissue volume. The volume in the areas between the 2-D slices can be extrapolated from the data associated with adjacent slices.

An HFU imaging component capable of generating 2-D slices as described herein is known in the art and therefore will not be described here in detail. However, a brief explanation of the HFU imaging modality implemented by such systems is provided to facilitate an understanding of certain embodiments described herein. When an HFU sound wave is incident on an interface between two tissues, a portion of the sound is reflected back into the original medium as a result of differences in acoustic impedance as between the two tissues. Increased differences in impedance as between tissues forming the interface will result more acoustic energy being reflected at the interface. As is known, acoustic impedance is a property of a tissue defined as density of tissue and velocity of sound in that tissue. So the HFU imaging system captures information concerning structure and density of imaged cells at different skin depths. More particularly, the HFU imaging modality can facilitate differentiation of cells based on their density. Cells in skin tissue that are associated with a lesion will have a different density as compared to healthy cells. Accordingly, the location and boundaries of a lesion can be identified in an image using the HFU imaging modality.

The HFU imaging modality can identify the presence of a lesion and its boundaries but can be inadequate to identify the biological nature of the lesion. For example, the HFU imaging modality can be inadequate to identify whether a particular lesion is a basal cell carcinoma (BCC), a squamous cell carcinoma (SCC) or a melanoma. The HFU can also be inadequate to differentiate between a skin cancer of some type and a mole or macule. In order to overcome this limitation, a second imaging methodology is used.

The second imaging methodology is an optical imaging method advantageously selected to facilitate the visualization of functional data associated with the cells which are being imaged. According to one aspect, the optical imaging methodology can be chosen to facilitate the optical acquisition of a two-dimensional image at one or more different skin depths. Accordingly, functional imaging data for a particular skin cancer can be acquired at a surface of the skin and/or at one or more different subcutaneous layers or depths beneath the surface of the skin.

According to one aspect, the optical imaging methodology is a spectroscopic imaging method. For example, the optical imaging methodology can comprise a multispectral imaging method that captures image data at a plurality of optical frequencies. Such multispectral imaging can include optical energy from the visible portion of the light spectrum but can also include optical energy from frequencies beyond the visible light range (e.g. infrared and near ultraviolet). Alternatively, the optical imaging methodology can comprise hyperspectral imaging wherein optical information is captured from across the electromagnetic spectrum at each pixel in the captured image. As a further alternative, the spectroscopic imaging method can comprise Raman spectroscopy which captures changes in the frequency of photons in monochromatic light which result from interaction with skin tissue.

The nature of a particular skin lesion will be consistent throughout the lesion, so it is not necessary to capture the functional data associated with the cells at all depths. Once the type of cancer has been determined using the second imaging methodology, all of the cells which are identified as being associated with the lesion can be marked accordingly. As noted above, the UHF imaging can differentiate such cells as having a density different from adjacent healthy/normal skin cells. Accordingly, in a subsequent data fusion process, the cells having a first density associated with a cancerous lesion can be highlighted, marked or otherwise displayed in a certain way to differentiate them from the adjacent healthy skin cells. For example, the cancerous skin cells can be displayed in a different color as compared to normal skin cells.

More particularly, the second imaging methodology described herein can be configured so that normal healthy skin cells are presented in a first color in displayed images which are presented to a user. For example, normal cells can be displayed in a green color. Cancerous cells can be presented in a different color from healthy cells. The particular color of the cancerous cells can correspond to the type of cancer which has been imaged. For example, BCC cells could be presented in yellow, SCC cells could appear blue, and melanoma cells could be presented in red.

The imaging data acquired using the first and second imaging methodology is provided to a computer workstation, such as a radiation therapy planning (RTP) workstation. Thereafter, within the RTP workstation the HFU imaging and the optical imaging is registered and then combined or superimposed to obtain a hybrid image. The workstation will use the images from the first and second image source to create a hybrid HFU/optical image that will represent a skin cancer. Cancerous cells having a different density from healthy cells can be rendered in a color corresponding to the particular type of cancer that has been detected. The image can represent the cancer in three dimensions, in a plurality of cross-sectional views and/or in a pseudo-three dimensional representation of a skin volume comprised of two dimensional image slices taken along two separate orthogonal axes.

In some embodiments, the second imaging methodology described herein can comprise biomarker optical imaging (BOI). Various types of BOI imaging methods can be used for this purpose. Biomarkers are well known in the art and therefore will not be described here in detail. However, it should be appreciated that any suitable biomarker can be selected for this purpose provided that it is responsive to the particular type of functional tissue sought to be identified. Likewise, the biomarker can be administered to a patient by any suitable means. For example, the biomarker can be applied topically, injected hypodermically at the site of a suspected cancer, or administered intravenously. With BOI, a biomarker (typically a fluorescent biomarker) is used that emits photons when a certain chemical/biological response or compounds are present. For example, a biomarker could identify high metabolic rate or a specific receptor based on its fluorescent activities or release of photons. An optical imager can be used collect those photons and form an image. The biomarkers used for the purposes of the imaging described herein are advantageously selected so that a cancerous skin lesion will appear to light up or illuminate in captured images so that the cells can be more easily identified when imaged using the second imaging method as described herein.

BOI imaging as described herein can facilitate graphically representing an area in which malignant cells are present. BOI imaging methods and systems are known in the art and therefore will not be described here in detail. However, it will be appreciated that the BOI imaging can be obtained using any type of biomarker and any suitable type of imaging system to capture the image. An RTP workstation for cutaneous oncology ("CO") will accept the BOI images as input.

Other scanning or imaging methods can also be used to facilitate understanding of the anatomy or structural characteristics of the cancer. These methods can be used in place of or in addition to the HFU imaging methods described herein. For example, such methods can include relatively simple laser scanning techniques such as LIDAR (Light Detection and Ranging). Alternatively, more complex scanning methods such as Optical Coherence Tomography (OCT) can be used to obtain detailed structural data associated with the cancer. Unlike LIDAR, it will be appreciated that OCT can penetrate beneath the epidermis. Of course, OCT has some limits with regard to how deep it can penetrate beneath the epidermis, but it can provide a very detailed view of the topology and the anatomy and in some scenarios could be used in place of HFU imaging as described herein. Once a skin cancer has been imaged using the hybrid imaging methods described herein, it can be displayed to a treatment specialist for analysis.

Once visualization of a lesion is provided as described herein, the next step is to facilitate radiation therapy planning to eliminate the cancerous cells. According to a further aspect, this planning process can be facilitated by providing the treatment specialist with a visual understanding of a radiation dose to be applied in combination with the hybrid imaging described herein. In this regard, it will be appreciated that each device used for delivery of radiation therapy to a patient will have a radiation output profile which is determined by various factors, such as the characteristics of radiation filters that are used. This radiation characteristic will generally be unique to each particular radiation therapy device or machine. As an example of the kind of radiation characteristic being described herein, a particular radiation characteristic can define how much of a radiation dose delivered by a particular radiation therapy machine will be delivered to tissue as a function of penetration depth. Such a characteristic is sometimes presented graphically and is referred to as a Percentage Depth Dose ("PDD") plot. As will be appreciated, a radiation output profile such as PDD can be very important to a practitioner who needs to understand how applied radiation from the machine will interact with the tumor at various skin depths.

Consequently, once a skin cancer has been imaged using the hybrid imaging methods described herein, it is advantageous to display the hybrid image (in two-dimensions or three-dimensions) to a treatment specialist together with a superimposed scaled graphical representation of the radiation profile (e.g. a PDD profile) of a radiation therapy device which will actually be used to administer the radiation treatment. In this way, the treatment practitioner can visually evaluate the dose of radiation that will be delivered to various portions of the cancer as displayed, when using a particular radiation delivery device. In some scenarios, the radiation delivery device can comprise an available component of an RTP workstation as described herein. Accordingly, the visual display can align the PDD profile along a vector axis corresponding to an alignment of a radiation therapy beam which is anticipated for use in a particular scenario. The beam alignment or vector direction can be manually input into the RTP, but in many scenarios it can be advantageous to provide a machine for applying radiation therapy in data communication with the RTP such that the RTP can receive information about radiation applicator position and thereafter present the proposed vector direction of applied radiation particles in accordance with a detected position of the radiation applicator.

According to a further aspect relating the treatment planning, a treatment practitioner can create a shield to protect portions of a patient's body from radiation to be applied by a radiation therapy applicator. Such a shield will have a cutout portion which will usually correspond to the shape of a cancer to be treated plus some additional margin around the cancerous tissue. According to a further aspect of the inventive arrangements described herein, an image of the shield including the cutout portion can be acquired and provided to an RTP as described herein. For example, a camera disposed in a radiation applicator unit can capture the image of the shield. The shield image can then be used as described below when visualizing a radiation treatment plan.

In particular, a three-dimensional pattern of radiation can be synthesized or rendered by an RTP workstation whereby the three-dimensional pattern is an irregularly shaped volume determined in accordance with the shield image and vector angle of applied radiation. Consequently, the three-dimensional pattern can visually show where radiation will be applied to underlying tissue as a result of the function of the shield. The irregularly shaped radiation pattern can be superimposed on a previously acquired two-dimensional or three-dimensional hybrid image of the cancerous cell as described herein. The resulting image or three-dimensional model is presented to a treatment specialist on a display device of the RTP so it can be observed. The treatment specialist can then visualize a resulting three-dimensional pattern of radiation which will extend through the skin tissue with the current shield and applicator setup. The shield can then be evaluated to determine whether the cancerous cells at each skin depth are being properly dosed with radiation in accordance with a potential treatment plan.

As will be appreciated, the three-dimensional beam pattern generated by the RTP for visualization purposes will depend in part on a beam alignment or vector direction of a radiation beam applied to the tissue and screened by the shield. Accordingly, the RTP can receive information about radiation applicator position and beam vector direction. Thereafter such information can be used by the RTP to determine and render the pattern and extent of the three-dimensional volume of applied radiation (for visualization purposes). Such pattern can then be displayed in accordance with such vector direction of radiation to be applied, superimposed over the image of the cancer as described herein. According to a further aspect, the visualization obtained by using the shield can be combined with the graphical display of radiation penetration plot (such as the PDD).

According to a further aspect, the three-dimensional representation of the radiation beam resulting from a particular shield pattern and beam vector can also be automatically evaluated by the RTP machine to determine whether all areas of the cancer are being adequately treated. For example, portions of the cancerous cells that are determined to receive an inadequate dose of radiation can be highlighted in a different color to show the deficiency of the resulting three-dimensional beam patter.

According to a further aspect, the RTP can determine an optimal shield pattern based on a selected vector and the hybrid three-dimensional image of the cancer. The optimal shield pattern, including appropriate margins around the cancerous cells can then be rendered as a two-dimensional pattern. The two dimensional pattern can be output by the RTP in an image format that is suitable to facilitate manually marking and cutting a metal plate which can be used as a shield or template in accordance with a radiation therapy treatment. Alternatively, the RTP can output the shield pattern in a data file format which is suitable for controlling a fabrication machine. In some scenarios, the fabrication machine can be included as part of the RPT workstation. One example fabrication machine that can be used for this purpose can include a tabletop computer numerically controlled (CNC) router (e.g., a CNC machine). However, the embodiments are not limited in this regard and the fabrication machine can also comprise a 3D printer. Thereafter, the fabricated shield or template can be fabricated so that it is available for use in treatment of a patient.

The various aspects disclosed above will be described with respect to the attached drawings of an exemplary system that can deliver both diagnostic and therapeutic functionalities through a single platform and an integrated workflow to better serve and benefit the practitioner and patient with skin cancer and/or skin lesions. The exemplary system provides multiple imaging devices and a radiotherapy device used cooperatively to diagnose, treat and verify treatment in accordance with the present disclosure. Thus, the system can be an image-guided superficial radiotherapy treatment system. The system includes software to analyze and combine data and images produced by the imaging devices to provide pinpoint and focused treatment with the radiotherapy device. Additionally, the diagnostic protocols can be repeated throughout the treatment process to adjust, focus, increase or decrease radiotherapy as appropriate.

FIG. 1 illustrates a high level view of an exemplary system 150 in accordance with the present disclosure and its main sub-modules. The exemplary system 150 can include a radiotherapy component 101 with X-ray tube 100, a solid-state X-ray beam sensing component 102, an ultrasound component 103 with a transducer 104, an optical imaging (OI) component 109 with an associated image capture device (ICD) 110. The system also includes a system control component 105 for guiding the radiotherapy of the radiotherapy component 101 based on images and data obtained from the ultrasound component 103, transducer 104, OI component 109, and ICD 110. The system control component 105 can also work with the solid-state X-ray beam sensing component 102 to ensure that the radiotherapy is of the appropriate intensity, depth and size. In some embodiments, the system can further include a template or shield fabrication component 111.

The ultrasound component 103 can include control circuitry, system drivers, operation control software, and a transducer 104, which can be high frequency ultrasonic transducer, for superficial epidermis, dermis-level and/or subcutaneous tissue anatomical imaging. The ultrasound component 103 communicates with the software of the system control component 105 via a bus and system drivers. The ultrasound component 103 and transducer 104 are provided in exemplary system 150 to provide structural or anatomical data without exposing a subject to ionizing radiation. However, the present disclosure contemplates that ultrasound component 103 and transducer 104 can be replaced or supplemented in system 150 with components for supporting any other types of imaging techniques that also do not utilize ionizing radiation. For example, optical coherence tomography or laser range scanning (LIDAR), to name a few.

The optical imaging component 109 can include control circuitry, system drivers, operation control software, and an image capture device 110, for superficial epidermis, dermis-level and/or subcutaneous tissue functional imaging. According to one aspect, the optical imaging component is a spectroscopic imaging device. For example, the optical imaging component can comprise a multispectral imaging device that captures image data at a plurality of optical frequencies. Such multispectral imaging component can be configured to utilize optical energy from the visible portion of the light spectrum for imaging purposes, but can also utilize optical energy from frequencies beyond the visible light range (e.g. infrared and near ultraviolet). Alternatively, the optical imaging component can comprise a hyperspectral imaging device wherein optical information is captured from across the electromagnetic spectrum at each pixel in the captured image. As a further alternative, the spectroscopic imaging device can be configured for Raman spectroscopy which captures changes in the frequency of photons in monochromatic light which result from interaction with skin tissue.

The optical imaging component 109 communicates with the software of the system control component 105 via a bus and system drivers. The present disclosure contemplates that optical imaging component 109 and the image capture device 110 can be replaced or supplemented in system 150 with components for supporting any other types of imaging techniques for extracting molecular or functional information from tissues. For example, biomarkers can be used to enhance the usefulness of the optical imaging methods described herein. As is known, a biomarker can involve a substance which is introduced to a tissue to facilitate the identification of a disease condition such as cancer. According to one aspect, a biomarker can include any substance introduced to a skin tissue which can be used to induce visually or optically detectable changes that can facilitate identification of cancerous cells. Any biomarker now known or known in the future can be used in conjunction with the optical imaging component 109 and image capture device 110 provided that it can help facilitate identification of functional data pertaining to skin tissue under observation.

The radiotherapy component 101, which can be a superficial radiotherapy component, and X-ray tube 100, can together include control circuitry, one or more cooling elements for the x-ray tube, power supplies, one or more high voltage generator, one or more interchangeable aluminum (Al) filter magazines, one or more collimating applicators, and one or more hardware timers that work in concert with a software timer for redundancy and other purposes.

It is contemplated that the X-ray tube utilized herein will be selected so that is optimize for superficial cutaneous interaction with skin tissue, and has minimal effects at deeper tissue depths. For example a conventional superficial radiation therapy (SRT) type of X-ray unit can be used for this purpose. As will be appreciated, an SRT type of X-ray unit produces low energy X-rays that are suitable to treat skin conditions as hereinafter described.

The solid-state X-ray beam sensing component 102 can monitor the beam output of the radiotherapy component 101 and x-ray tube 100, along with overall system stability and yield. The solid-state X-ray beam sensing component 102 is mounted underneath the X-Ray tube 100 and is moved in front of the tube when the system 150 needs to be tested for quality control, or overall system 150 diagnosis purposes. Otherwise, it is retracted back in its home position, away from the X-ray tube 100 and the X-ray beam in order not to interfere during a normal operating mode.

The present disclosure contemplates that in addition to or as an alternative to using a X-ray based radiotherapy in system 150, any other types of radiotherapy can be used in system 150. Thus, the components for radiotherapy can be selected to support photon-based radiotherapy (e.g., x-rays and gamma rays), particle-based radiotherapy (e.g., electrons, protons, neutrons, carbon ions, alpha particles, and beta particles), or any combinations thereof.

In an exemplary operation, the system 150 utilizes the ultrasound component 103 with a transducer 104 to scan and image a tissue volume of interest, such as a volume of the skin with a lesion, to obtain structural or anatomical information about the region of interest. The system then utilizes the optical imaging component 109 with image capture device 110 to optically scan and image the same volume to obtain functional and/or metabolic information pertaining to the skin tissue or portions thereof. As used herein, the functional and/or metabolic information referenced herein can include any information pertaining to the biological function, behavior or processes at work in a particular cell or group of cells. The ultrasound and optical scanning processes will be described below in further detail. However, it should be understood that each scanning method will advantageously provide image data sufficient in combination to produce a three-dimensional representation of the scanned volume of tissue. In some scenarios, the three-dimensional representation produced by the ultrasound and optical image scanning methods described herein can each individually comprise a plurality of two-dimension image slices taken along one or more orthogonal axes, which can be combined to form a three-dimensional image.

A registration process is used to facilitate alignment of the image data acquired using the ultrasound and optical scanning methods. After the region of interest has been scanned and imaged by the system 150, the image data is processed by the system's software. The image data acquired using the ultrasound and optical scanning methods can be registered and then fused or merged to form a single image. In the fused image, the image data acquired by using ultrasound is basically superimposed over the image data acquired by using the optical scanning method described herein. The result is a hybrid image which includes detailed anatomical and/or structural data for the skin cancer with the functional data for the same tissue volume superimposed.

The system 150 can be used to analyze and quantify the tumor and subsequently prepare a treatment plan that is derived from the actual tumor parameters, such as volume, circumference, penetration depth, and tissue density. Once the tumor analysis and quantification are complete, the system 150 software provides analytical guidance to deliver the most accurate and appropriate superficial radiotherapy pertaining to the scanned and analyzed tumor. The therapy is then delivered by the integrated superficial radiotherapy component 101. The system's software documents the entire diagnosis and treatment cycle and archives the patient data on a patient data repository 107 and the overall system 150 functionality log on a system data repository 108.

The superficial radiotherapy component 101 can be utilized to treat any tumors, lesions or areas where analysis or diagnosis determines that treatment is needed. The superficial radiotherapy component 101 delivers collimated and focused x-ray photon particles to treatment areas. The treatment can be without any biopsies and the pre-treatment analysis, treatment and post-treatment analysis can be carried out locally without the need for remote sources or analysis. The level of treatment can be determined as set forth below.

The system 150 is controlled and operated by the system control component 105, which can include a central computer with a motherboard that runs operation and control software with various parallel and connected boards that allow it to control, communicate, and monitor the various sub-components and modules of the system 150. This achieves harmonious functionality between the two main clinical components of the system 150, the superficial radiotherapy component 101, which provides radiotherapy treatment, and the ultrasound component 103, which is utilized to scan and acquire the anatomy and topology of a patient's skin area of concern for further analysis, diagnosis, quantification, and therapy planning purposes. The system control component 105 can be connected with data repositories, including a patient data repository 107 and a system data repository 108. The system 150 can also be connected to a network 106, such as a local area network, a wide area network and/or the Internet, which allows for clinical and system data exchange with remote systems or networks.

The system control component 105 can be configured to output a two dimensional pattern for a template or shield to be used during radiation treatment for masking or shielding certain portions of a patient's skin. The two-dimensional pattern can be output to a user in the form of an image or pattern that is suitable to facilitate manually marking and cutting a metal plate which can be used as a shield or template in accordance with a radiation therapy treatment. Alternatively, the control component 105 can output the shield pattern in a data file format which is suitable for controlling a fabrication machine. In some scenarios, a fabrication machine 111 can be included as part of the system 150. One example of a fabrication machine 105 that can be used for this purpose can include a tabletop computer numerically controlled (CNC) router (e.g., a CNC machine). However, the embodiments are not limited in this regard and the fabrication machine 111 can also comprise a 3D printer that is capable of 3D metal printing. Thereafter, the fabricated shield or template can be fabricated by the fabrication machine 111 so that it is available for use in treatment of a patient.

The patient data repository 107 and the system data repository 108 can be a solid-state drive, hard drive or other memory device. The patient data repository 107 can store patient-related data and treatment parameters, such as patient records, treatment session chronology, and disease documentation and photos. The system data repository 108 stores all system-related data and parameters, such as the system log, x-ray calibration data, and system diagnostics results. The patient data repository 107 and the system data repository 108 can be discrete devices or physically combined. One or more partitions can be used if the repositories 107 and 108 are combined, such as a single repository.

Figure 2:
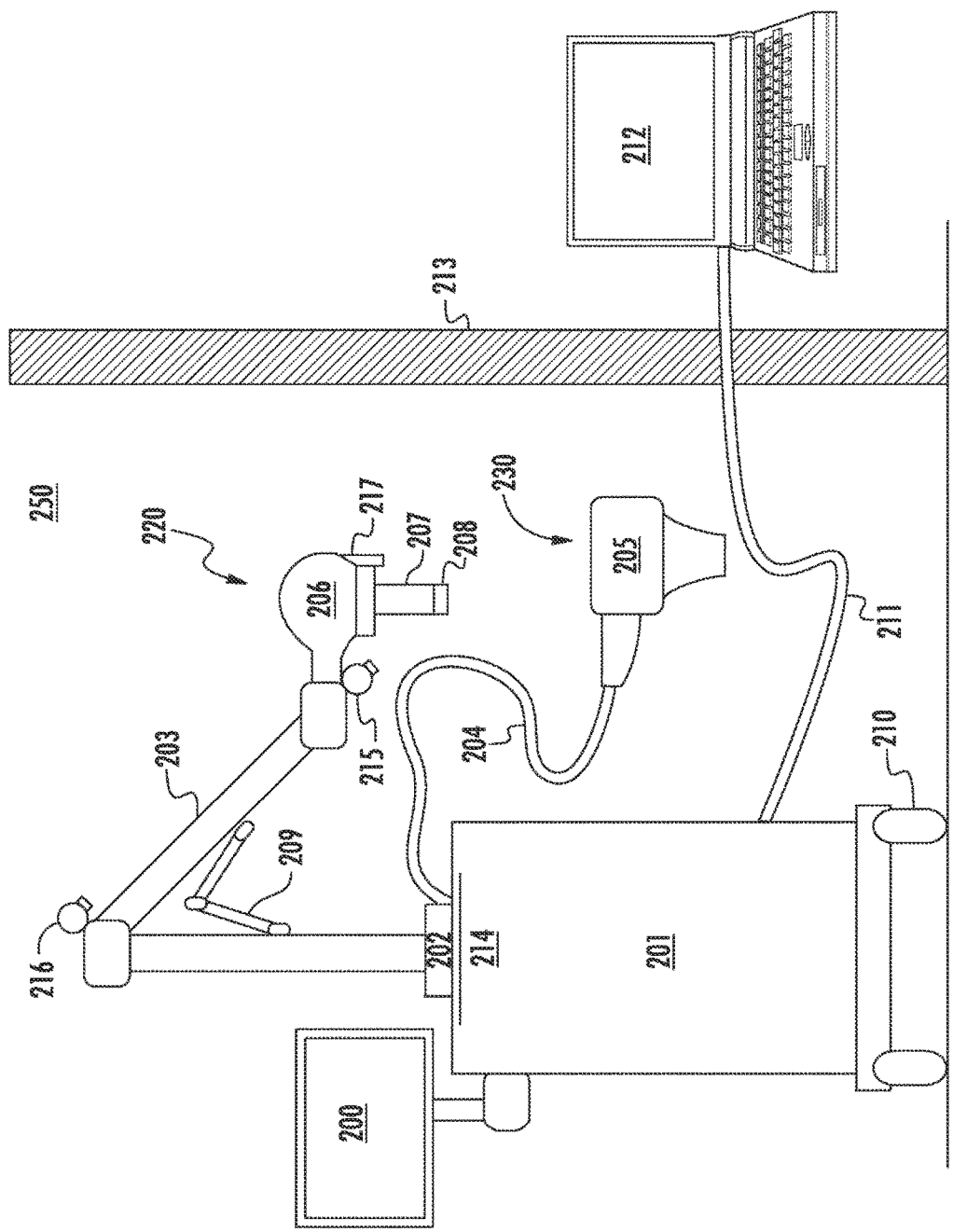
FIG. 2 is an exemplary embodiment of an image-guided radiotherapy system.

One embodiment of an ultrasound guided radio therapy treatment and diagnostic system 250 is shown in FIG. 2. The system 250 can include a base unit 201 with various components mounted thereon or connected therewith. These components can include a radiotherapy treatment device 220 and its various components and an imaging subsystem 230.

The base unit 201 can be typically a compact unit such as one with a 30"×30" footprint and can be mounted on casters 210 for ease of maneuverability. The base unit 201 can include a power lead for optionally providing power to all of the components housed in or connected to the base unit 201. In this regard, the base unit 201 can contain one or more computers for controlling the system 250 components and/or analyzing and processing data obtained from the system 250 components. A monitor 200 can also mounted to the base unit 201 for a user interface. Likewise, a terminal or an input device 214, such a as keyboard or mouse, can be included.

A mount 202 is provided on the base unit 201 for mounting the radiotherapy treatment device 220. The radiotherapy treatment device 220 can include a treatment arm 203 and treatment head 206, which can include removable or movable applicators 207, 208. The treatment arm 203 is articulated with appropriate retractable articulations 209. Although not shown in FIG. 2, additional articulations can also be provided at different points of system 250 to increase a number of degrees of freedom of placing and orienting treatment head 206. For example, additional articulations can be provided between treatment arm 203 and treatment head 206 and between mount 202 and treatment arm 203. Moreover, the number of articulation points illustrated in FIG. 2 is solely for ease of illustration. The present disclosure contemplates that the any number of articulation points between mount 202 and treatment head 206 can be provided so as to provide any number of degrees of freedom in treatment arm 203 required positioning and orienting the treatment head with respect to the patient.

A camera 216 can also be included to provide for remote operation or for documentation of treatment. A video-laser positioning system having camera 215 and laser or light pointer 217, which visibly marks a region with a crosshair that will receive radiotherapy treatment, can be provided. The camera 215 can capture low opacity images of the radiotherapy treatment head 206 and crosshairs of laser pointer 217 during treatment so that the exact positioning and orientation can be reproduced during subsequent treatments. In this regard, the video-laser positioning system can identify proper and precise positioning and orientation of treatment head 206. The video-laser positioning system can also allow for remote control and operation of the treatment arm 203 so that the treatment head 206 can be positioned precisely while the user is remote. In operation discussed below, the treatment arm 203 can be articulated and positioned to allow the treatment head to apply radiotherapy to a patient.

The imaging subsystem 230 can include at least one imaging head 205 attached via a corresponding lead 204 to the base unit 201 and data acquisition and processing machinery housed therein. The imaging head 205 can be a compact hand-held unit tethered to the base unit 201 by the corresponding lead 204. As such, the imaging head 205 can be freely moved to facilitate scanning different skin locations on the body of a patient. In operation, the imaging subsystem 230 can be used to collect both images and data of a diagnosis or treatment area before, during or throughout and after treatment. In some arrangements, an imaging head 205 can be mounted on the arm 203 instead of being provided separately.

Each imaging head can include components needed for supporting an imaging modality. For example, referring back to FIG. 1, a first imaging head 205 can be provided that includes ultrasound component 103 and transducer 104 and a second imaging head 205 can be provided that includes optical imaging component 109 and image capture device 110. However, the present disclosure also contemplates combined functionality. That is, a single imaging head 205 can incorporate ultrasound component 103, transducer 104, optical imaging component 109, and image capture device 110.

Lead 211 can connect the system 250 to another computer 212 or use interface that can be positioned behind a shield 213 for remote operation of the system 250 or components of system 250, such as the radiotherapy treatment device 220.

Figure 3:
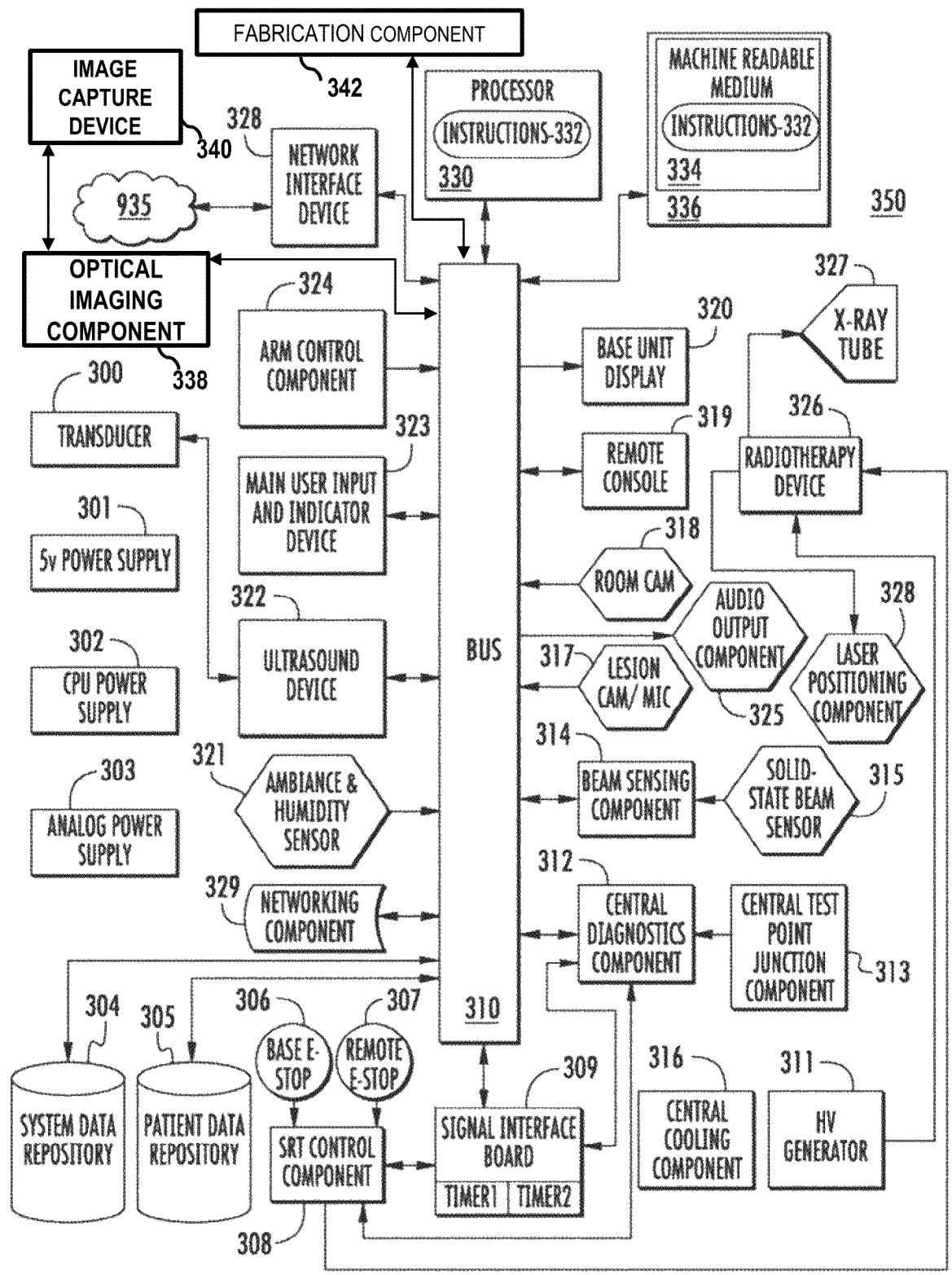
FIG. 3 is a schematic drawing of another embodiment of an image-guided radiotherapy system.

FIG. 3 illustrates a schematic view of various components and sub-components of RTP system 350. The system 350 can include a bus 310 through which the various components can communicate with each other and/or the processor 330 (e.g., a central processing unit (CPU), a graphics processing unit (GPU), or both). The processor 330 can be connected to the bus 310 as shown in FIG. 3 or integrated therewith. Power supplies 301, 302, 303 can also be included.

The system 350 can be controlled and operated by processor 330 that runs the system 350 software or instructions 332, which controls the system 350 functions, verifies the safety mechanisms, and the service and calibration functions. The processor 330 can be in communication with a machine-readable medium 334, which can be static memory 336, on which is stored one or more sets of instructions 332 (e.g., software) embodying any one or more of the methodologies or functions described herein, including those methods illustrated herein. The instructions 332 may also reside, completely or at least partially, within the system data repository 304, static memory, or within the processor 330, or a combination thereof, during execution thereof by the system 350. The system data repository and patient data repository and the processor 330 also may constitute machine-readable media.

The processor 330 can be in communication with a motherboard having an appropriate amount of static or dynamic RAM, such as 4 GB of DRAM, in order to optimally support and accommodate the operating system, main software, and real-time system monitoring functions, together with efficient patient and data system handling and archiving. The system 350 software also communicates with the peripheral components, such as Ethernet, USB, and audio/video or via network interface card 338 in order to implement the system's user/machine interface and exchange data with external workstations and data repositories, such as electronic medical records (EMR), electronic health care records (EHR), hospital information systems (HIS), radiology information system (RIS), and picture archiving and communication systems (PACS), utilizing digital imaging and communications in medicine (DICOM) and health level 7 (HL7) communications and data structure protocols.

The system 350 can include storage mediums 304 and 305, such as solid state drives, hard drives or the like. Storage medium 304 can be the system data repository, which can include the operating system, the main system software, and system data and parameters archive. Storage medium 305 can be the patient data repository 305, which stores all patient-related data and records.

The system 350 can include a base unit that houses or otherwise provides various components of the system 350, including user interfaces. The base unit can include a base unit display device 320, such as an LCD display, and a base unit user input and indicator device 323, such as a terminal or a mouse. The system 350 can also include a remote console 319 that can be used to remotely control the system 350 so that a user does not need to be present during radiotherapy treatment. The base unit user input and indicator device 323 allows the user to interact with the system 350. The base unit user input and indicator device 323 can be utilized for initial patient data setup on the system 350 and for the ultrasound imaging of the patient's tumor at various stages of the disease before, during, and after the superficial radiotherapy period. Furthermore, the base unit user input and indicator device 323 can also be a terminal of the system 350 software. The diagnostics results and images, patient data, remote workstations topology, patient and room monitoring data, system service menus, system physics and calibration menus, and all system queues and alerts can be displayed on the base unit display device 320 or via the base unit user input and indicator device 323 as appropriate.

The system 350 can also include an ultrasound device 322 with a transducer 300. The ultrasound device can obtain structural or anatomic images of the treatment area or skin lesion of concern. With the ultrasound device 322 with a transducer 300, diagnostics of the area of concern can be processed. The ultrasound device 322 can be any ultrasound device capable of operating within an acceptable bandwidth. For example, the high frequency ultrasound device 322 can operate in a bandwidth of approximately 20 MHz to approximately 70 MHz, and may be implemented with an electro-mechanical, or solid state transducer. The system 350 can provide the ultrasound imaging device 322 at least partially integrated inside a system 350 housing coupled to bus 310 with a transducer head outside of the housing as shown in FIG. 2. The ultrasound device 322, and other components of the system 350, can be in communication with the bus 310 and the respective other components of the system 350 utilizing interface standards such as peripheral component interconnect (PCI/PCIe), universal serial bus (USB/USBII/USBIII), or Firewire. However, the present disclosure contemplates that any other interface and/or communications standards can be used.

The system 350 can also include an optical imaging component 338 with an optical image capture device 340. An optical imaging component 338 can obtain functional images of a three-dimensional volume comprising a treatment area or skin lesion of concern. With the optical imaging component 338 and image capture device 340, image data representative of the treatment volume of concern can be obtained and processed.

The optical imaging component 338 can include any type of image capture device now known or known in the future. According to one aspect, the optical imaging component can comprise an electronic image capture device 340 that captures incoming photonic radiation and converts same into electrical signals. An image capture device of this type can be comprised of a focusing element (e.g. a lens), a charge-coupled device (CCD) or a CMOS image sensor, and readout circuitry for acquiring the image data. Image capture devices as described herein are well known and therefore will not be described here in detail.

The system 350 can provide the optical imaging component 338 at least partially integrated inside a housing of system 250 coupled to bus 310 with an image capture device 340, outside of the housing as shown in FIG. 2. The optical image component 338 and other components of the system 350 can be in communication with the bus 310 and the respective other components of the system 350 utilizing interface standards such as peripheral component interconnect (PCI/PCIe), universal serial bus (USB/USBII/USBIII), or Firewire, to name a few. However, the present disclosure contemplates that any other interface and/or communications standards can be used.

The system 350 can further include a radiotherapy device 326 that includes an SRT X-ray tube 327. As discussed herein, the radiotherapy device 326 that includes an X-ray tube 327 can deliver radiation therapy to a particular region or area on a patient. The radiotherapy device 326 can be coupled with a high voltage generator 311 and a central cooling component 316.

The system 350 can also include a control component, such as superficial radiotherapy control component 308, for controlling the radiotherapy provided by radiotherapy device 326. The superficial radiotherapy control component 308 can control aspects of the radiation dosage, including timing, depth and intensity. In this regard, an arm control component 324 can also be provided with the system 350 and in communication with the superficial radiotherapy control component 308 and/or processor 330. The arm control component 324 can move, articulate or otherwise control positioning of the arm to which the radiotherapy device 326 and x-ray tube 327 are mounted. A base e-stop 306 and remote e-stop 307 can also be provided to provide local and remote emergency termination functions so that the radiotherapy device 326 can be stopped either locally or remotely.

Additionally, solid state beam sensing component 314 with a solid-state beam sensor 315 can be provided. In one embodiment, these components can be housed within the housing of X-ray tube 327. The solid state beam sensing component 314 with a solid-state beam sensor 315 provide the ability to obtain on demand and local analysis of the radiotherapy device 326 with X-ray tube 327. Utilizing the solid state beam sensing component 314 with a solid-state beam sensor 315, the radiotherapy device 326 with X-ray tube 327 can be tested to determine if the radiation output is consistent with the desired radiation output. In the event that there are discrepancies, the devices can be re-calibrated or otherwise serviced.

A central diagnostics component 312 can also be provided and can be interfaced with bus 310 and processor 330. The central diagnostic component 312 is also connected with a central test point junction conjunction 313 and additionally interfaces with a signal interface board 309 that is in turn connected to both the processor 330 through bus 310 and the superficial radiotherapy control component 308. The signal interface board 309 can also include a first and second timer for redundant time counting during the application of radiation therapy, which provides for added patient safety and accurate dosimetry calculation for the delivered therapy dose to the patient. In addition to the dual hardware timers, one or more additional software based timers can be utilized or invoked by system 350.

The central diagnostics module 312 is a systems diagnostic component that monitors the various system boards and components for failures and/or errors. The central diagnostics module 312 can generate alerts regarding the system status that can either be communicated with the user, or with the system installer or manufacturer for maintenance purposes.

Additional inputs can be connected to the processor 330 through bus 310 including a camera and/or microphone 317, an audio output component 325, such as a speaker, a room camera 318 for taking pictures or video of the patient, treatment areas and/or the treatment process. An ambiance and humidity sensor 321 can also be provided in the event that conditions may affect the treatment or any of the system 350 components. However, the arrangement is not limited in this regard. A fabrication component 342 for fabrication of a metal shield or template can also be connected to the bus 310 in some embodiments.

FIG. 4A illustrates an exemplary process 450 with at least one imaging device 400, along with subsequent a tumor processing, rendering and analysis method and process 450. As an example, the method and process 450 can be used with systems 150, 250 and 350, and their software that can be integrated with or operatively in communication with various system components as shown in FIGS. 1-3.

As shown in FIG. 4A, an ultrasound head or device 400 includes an ultrasound transducer 401 located in the head 400. High frequency ultrasound is used for the imaging, which provides a much clearer image in comparison to low frequency ultrasound, but which does not penetrate deeply into the skin. High frequency ultrasound can include frequency ranges of approximately 20 MHz to approximately 70 MHz, such as approximately 35 MHz to approximately 55 MHz.

In operation, the method and process 450 can begin with obtaining ultrasound image data. Using imaging device 400, an ultrasound beam 402 is aimed at an area of concern, such as lesion 403, through the epidermis 404, dermis 405 and subcutaneous fat 406. In use, the transducer 401 sends high frequency ultrasonic waves towards the epidermis 404, dermis 405, and subcutaneous tissue 406, where the tumor 403 is located in varying depth, circumference, and volume. The reflected ultrasonic waves 402 that hold the tumor's physical characteristic data (structural/anatomical data) are acquired by the transducer 401. For example, the structural/anatomical data collected can include a density characteristic of the tissue which is being imaged. A lesion will have a density that is different from surrounding healthy tissue and can therefore be easily differentiated within the captured image data. The difference in density can allow the location and boundaries of the lesion to be determined. As an example, a non-melanoma skin cancer lesion 403 is located as shown, and the lesion 403 may extend away from the epidermis 404 and into the subcutaneous fat 406.

Data and images 419 obtained by the ultrasound device 400 are acquired by an image data acquisition component at step 407 and pre-processed for further processing, as shown with the flow diagram of FIG. 4A. The image data acquisition 407 can be followed by processing at central processing unit (CPU) at step 408, in which the CPU processes the raw data captured by the image data acquisition at step 407. Thereafter, at step 409, the central processing unit can execute instructions of software to process the data to create and render 2-dimensional (2D) images, which are acquired in slices across the area imaged by the ultrasound device 400. As an aid to understanding, steps 407, 408 and 409 are graphically illustrated at 414, 415, and 416.

The data and images obtained by the ultrasound device comprise structural data that is useful for representing the skin cancer lesion 403. At 427-429, functional data is also obtained for the skin cancer lesion 403. The functional data can be acquired using an optical imaging component as described herein. Such optical imaging component can comprise a separate image capture head or can be incorporated into the imaging device 400 so that both types of image data can be captured concurrently. Accordingly, the acquisition of functional data can begin at 427 with the acquisition of raw image data. The process can continue to 428 where the central processing unit can execute instructions in software to process the data so as to create or render a 2-dimensional image at 429.

Steps 427-429 can involve performing optical imaging using a spectroscopic imaging device to obtain a two-dimensional optical image 413. For example, the optical image can be obtained by using a technique such as multi-spectral imaging, hyperspectral imaging and/or Raman spectroscopy to capture and generate two-dimensional biological or functional image data for the tumor.

The process continues at step 410, which involves fusing the structural data obtained in steps 407-409 and comprising the 3D model, with functional data obtained in steps 427-429. This step is graphically shown in 417, which shows that the optical image 413 obtained in steps 427-429 can be a two-dimensional image which corresponds to an image plane that is essentially orthogonal to the two-dimensional image slices 419 comprising structural data obtained using high-frequency ultrasound. The image plane corresponding to the optical image 413 will generally correspond to the outer surface of the skin tissue. The nature of a particular skin lesion will be consistent throughout the lesion, so it is not necessary to capture the functional data associated with the cells at all skin depths.

According to one aspect, registration/location information associated with the optical imaging in step 427 and the image acquisition in step 407 can be utilized to fuse the optical image data with the 3D model. Thereafter, the model can be updated or enhanced to indicate both structural and functional information regarding the tumor. Methods for image registration are well known in the art and therefore will not be described in detail. However, it will be appreciated that the two images can be registered by using techniques involving fiducials or pattern recognition methods.

Once the images are registered, the information they contain can be combined into the fused 3D model. This can be done in a variety of ways. In some configurations, the structural image data can be provided in grayscale and the functional image data can be provided as a color overlay to indicate the functional information. In another configuration, the structural image data can be provided in grayscale or color and the functional information can be used to adjust the data in the structural image data. For example, the function information can be used to attenuate one or more color properties of data in the structural image data.

As noted above, the UHF imaging can differentiate tumor cells as having a density different from adjacent healthy/normal skin cells. Accordingly, in a subsequent data fusion process, the cells having a first density associated with a cancerous lesion can be highlighted, marked or otherwise displayed in a certain way to differentiate them from the adjacent healthy skin cells. For example, voxels associated with the cancerous skin cells can be displayed in a different color as compared to normal skin cells.

Once biological/functional nature of the tissue comprising the lesion has been determined using the optical imaging methodology, all of the cells which are identified as being associated with the lesion can be marked accordingly. Therefore, the image combining step can involve evaluating each voxel associated with the 3D model which was generated using ultrasound to determine whether a tissue density at particular voxel location differs from a density of healthy tissue at surrounding locations. If a particular voxel density at any skin depth corresponds to the lesion (e.g. cancerous tissue) then the voxel can be assigned a voxel color value associated with cancerous tissue. The voxel color can determine the color that the voxel is displayed as when rendered. But if a particular voxel density at any skin depth corresponds to healthy tissue, then it can be assigned a different voxel color value. Accordingly, the functional or biological information captured using a two-dimensional optical imaging technique can be extended or used to assign a color values to all of the voxels in the 3D model obtained by using ultrasound methodology. The result is a hybrid or fused 3D model containing information from both ultrasound and optical imaging methodologies.

Thereafter, when the fused 3D model is rendered, the cancerous skin tissue can appear as a different color as compared to the surrounding healthy skin tissue. The particular color chosen for the cancerous tissue can be determined by the type of cancer. For example, tissue identified as a BCC can be assigned the color yellow, tissue identified as an SCC can be assigned blue, and tissue comprising a melanoma can be assigned the color red. Accordingly, when the fused 3D model is rendered to a treatment specialist, the boundaries and type of lesion can be easily apprehended.

In some configurations, the resulting fused 3D model may not provide a "real world" representation of the tumor. That is, the color and other properties of the fused 3D model may not correlate with what a physician or diagnostician is accustomed to reviewing in a microscope slide or other specimen during a biopsy. Accordingly, the present disclosure contemplates that in some configurations, to ease review and treatment planning, an additional translation or transformation may be used. That is, a transformation matrix can be provided for converting the raw fused 3D model into a 3D model that visually corresponds to what a physician or diagnostician is accustomed to reviewing in a microscope slide or other specimen during a biopsy.

The fused 3D tumor model can be passed to the therapy module at 412, which can be hardware or software, for tumor analysis and therapy planning. The therapy module can be used to analyze the 3D tumor, structurally and functionally, and calculate the designated treatment area voxel, along with the pertinent dosimetry to be applied by a radiotherapy device. The dosimetry can include measurements and calculations of the absorbed dose in tissue resulting from the exposure to radiation. In one example, the appropriate treatment volume can be a spherical shape or a cylindrical shape. Alternatively, the appropriate treatment volume can be any other suitable shape that will leave appropriate treatment margins around the tumor. The accuracy provided by the hybrid imaging allows the treatment margins to be of the order of 10%, which is a significant improvement over the typical 300% treatment margins used in Mohs surgery.

Additionally at 412, appropriate therapy can be determined using the fused 3D model 418. The therapy software can include vector tables identifying the appropriate radiotherapy dosages for different sized tumors. This allows the system to precisely calculate therapy parameters, including treatment dosage based on the actual size of the tumor, including its depth and volume, rather than relying on the physician having to estimate the tumor size and depth based on experience and the visible surface area of the tumor.

From the foregoing discussion it will be understood that a hybrid or fused 3D tumor model or volumetric model can be rendered. A 3D construction and rendering engine can combine all or a portion of extracted 2D tumor slices obtained using ultrasound and optical imaging methods as described herein. The data from each scanning process can be merged and the system will fuse them into an integrated 3D model that represents and manifests the tumor's 3D anatomical and functional features. During the construction and rendering sequence, the 3D engine can apply geometrical corrections, smoothing and anatomical triangulation to the rendered 3D tumor model in order to achieve a correlation with the actual scanned or imaged tumor.

Figure 4B:
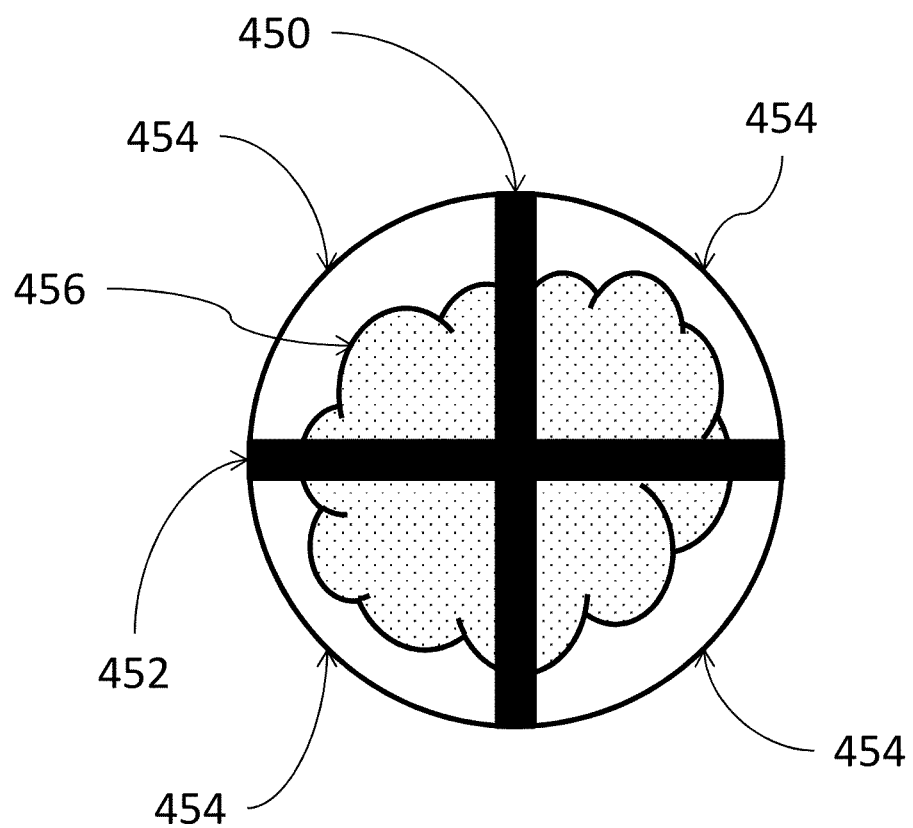
FIG. 4B illustrates an exemplary method for generating a 3D model of a tumor.

However, in some configurations it may not be desirable to acquire a large number of slices to generate the 3D tumor model. In particular, the 3D tumor model can be generated from two 2D slices, as shown in FIG. 4B. That is, a first slice 450 and a second slice 452, perpendicular to each other, can be selected. Thereafter, the volume in the areas between the slices 454 can be extrapolated from the data associated with the first slice 450 and the second slice 452 and an estimated 3D model of the tumor 456 can be generated. In some configurations, the edges of the tumor in the first slice 450 and the second slice 452 can be identified and the estimated 3D model of the tumor 456 can be generated from only the data in the first slice 450 and the second slice 454 associated with the tumor in these slices.

The process illustrated in FIG. 4B expedites the 3D modeling process as only limited 2D data is required to generate the estimated 3D model of the tumor. In some scenarios, treatment planning does not require a highly accurate 3D model of the tumor, in which case the estimated 3D model of the tumor 456 will suffice. However, the present disclosure contemplates that in other configurations that a similar process can be performed using any number of 2D slices. In either scenario, the physical image data and functional image data will be fused as described herein with respect to FIG. 4.

Figure 5:
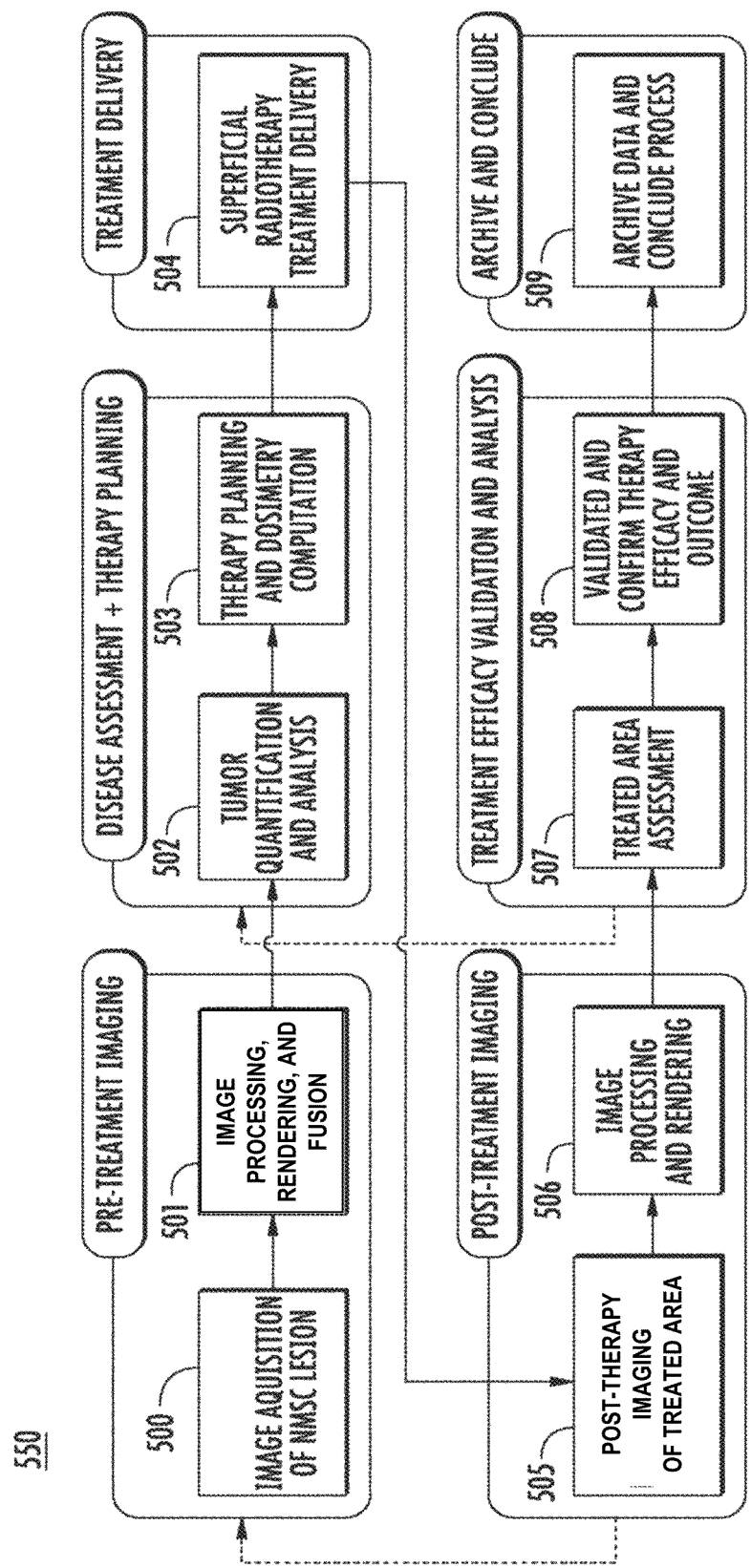
FIG. 5 is flow diagram of a method of diagnosis and treatment.

One embodiment of a method 550 of diagnosis, therapy planning, radiotherapy treatment, post treatment diagnosis and treatment validation and analysis is provided in a flow diagram of FIG. 5. Although the flow diagram illustrates the steps as sequential, the steps can be completed in different logical orders and some steps, or groups of steps, can be repeated as needed.

The method 550 can begin during a pre-treatment imaging stage at step 500 with image acquisition of an area of concern, such as a non-melanoma skin cancer (NMSC) lesion or a tumor. This is utilized to acquire the structural and functional parameters of the lesion or tumor. Acquired data and images are then transferred to the image processing, rendering, and fusion step 501. As noted above in reference to FIG. 4A and the corresponding discussion, image data regarding structural features is subject to image processing and rendering and combined with image data regarding functional or molecular features at step 501 to generate a 3D model of the tumor and, optionally, of surrounding tissues.

The method then moves on to a disease assessment and therapy planning stage starting at step 502. At step 502, the lesion or tumor in the 3D model is assessed, defined, quantified, and diagnosed. This can include any classifications for skin cancer type. The assessment at step 502 is based on both the structural and functional features of the 3D model. The 3D model provides a user, such as doctor or clinician, with a local means to diagnose the skin cancer type instead of using the time consuming and invasive biopsy method. However, the present disclosure contemplates that automated diagnosis systems can be utilized, with or without a user confirmation step. Such automated diagnosis systems can utilize, for example, pattern recognition techniques to identifying one or more portions of the 3D model exhibiting signs of disease.

Based upon the initial imaging and analysis data, including any classification as to a type of skin cancer, the clinician and patient can decide to proceed with superficial radiotherapy to treat the diagnosed skin cancer lesion. Thus, during the disease assessment and therapy planning stage, tumor quantification and analysis can also occur at step 502 to identify a suitable treatment volume for the tumor that provides acceptable margins. Based on the 3D model and the treatment volume, a tumor volumetric model is provided.

With the tumor volumetric model, therapy planning and dosimetry computation can occur at step 503. Therapy planning and dosimetry computation is carried out at step 503 where the data and images passed from step 502 can be further manipulated and analyzed, including analysis of the tumor and therapy factors. The therapy planning can include not only the dosimetry computation, but also planning for the best location on the skin to reach the center of the tumor and the best angle of presentation for the treatment head. To plan treatment, the 3D tumor model can be orientated in correlation to the anatomy of the area to be treated. Physiological, topographic, and radiation therapy dosimetry parameters can be applied to compute and design the treatment plan, beam targeting and guidance, including the treated area voxel. A fractionation scheme and treatment head positioning on the patient can also be determined. The treatment plan can then completed and loaded into a patient record and scheduler.

In some configurations, the treatment planning can involve generation of a mask or shield formed of a thin plate of material such lead. An exemplary mask or shield as described herein can be understood with reference to FIG. 6. As illustrated therein, an X-ray treatment head (e.g., treatment head 206) can comprise a housing 611 within which is disposed an X-ray tube 600. A Bremsstrahlung beam-hardening aluminum filter 607 can be disposed within the housing to control the X-ray beam 612 output from the x-ray tube 600. As shown, an X-ray beam aligned along a vector direction 658 can be applied by an applicator unit 609, which limits the overall cross-section of the beam. In order to further limit the amount of irradiated tissues, a mask 652 can be generated. The mask can be placed over the patient's body, where the mask includes an aperture or cutout portion 654. The cutout portion is sized and shaped to allow radiotherapy to be applied to a more limited area of the patient's body. The aperture or cutout area 654 is advantageously cut to the shape of the specific cancerous lesion but includes a further margin which extends a predetermined distance beyond the outer periphery of the cancerous cells. Only that portion of the X-ray beam that passes through the cutout will interact with the cancerous cells. Moreover, since the mask acts as a shield to radiation, high doses can be applied to the cancerous cells or lesion, since concerns with irradiating healthy tissues are significantly reduced.

According to one aspect of the invention, the aperture or cutout area 654 of the shield 652 can be designed based on the fused 3D hybrid image of the cancerous cells comprising the tumor. An RTP system (e.g. processor 330 associated with RTP system 350) can determine an optimal shield pattern based on a selected beam vector and the hybrid image of the cancer, which has been generated using the techniques described herein. Thereafter, the RTP system can provide a scaled shield pattern as a data output (e.g., output using a network interface device 328) to facilitate fabrication of an optimal shield for use in treatment. The shield can then be manufactured manually or by suitable automated means. For example, the data output data from the RTP system can be in a format suitable for a conventional Computer Numerical Control (CNC) type machine which uses a computer to control machine tools. Alternatively, the data output can be communicated to a 3D metal printer, capable of printing 3D metal parts. Consequently, the shield can be manufactured automatically and with high precision. In some configurations, where the treatment planning calls for radiotherapy to be provided at various angles, a different mask 652 can be provided for different angles or groups thereof, where the shape of the aperture 654 can be adjusted based on the 3D model and the radiotherapy angle to be used.

According to a further aspect, an image of the mask or shield 652 (including the aperture or cutout portion 654) can be acquired by an imaging device. The image can then be provided to an RTP as described herein. For example, an imaging device 656 disposed in a radiation applicator unit 609 can capture the image of the shield 652, including the aperture or cutout 654. The shield image can then be used when visualizing a radiation treatment plan.

Figure 7:
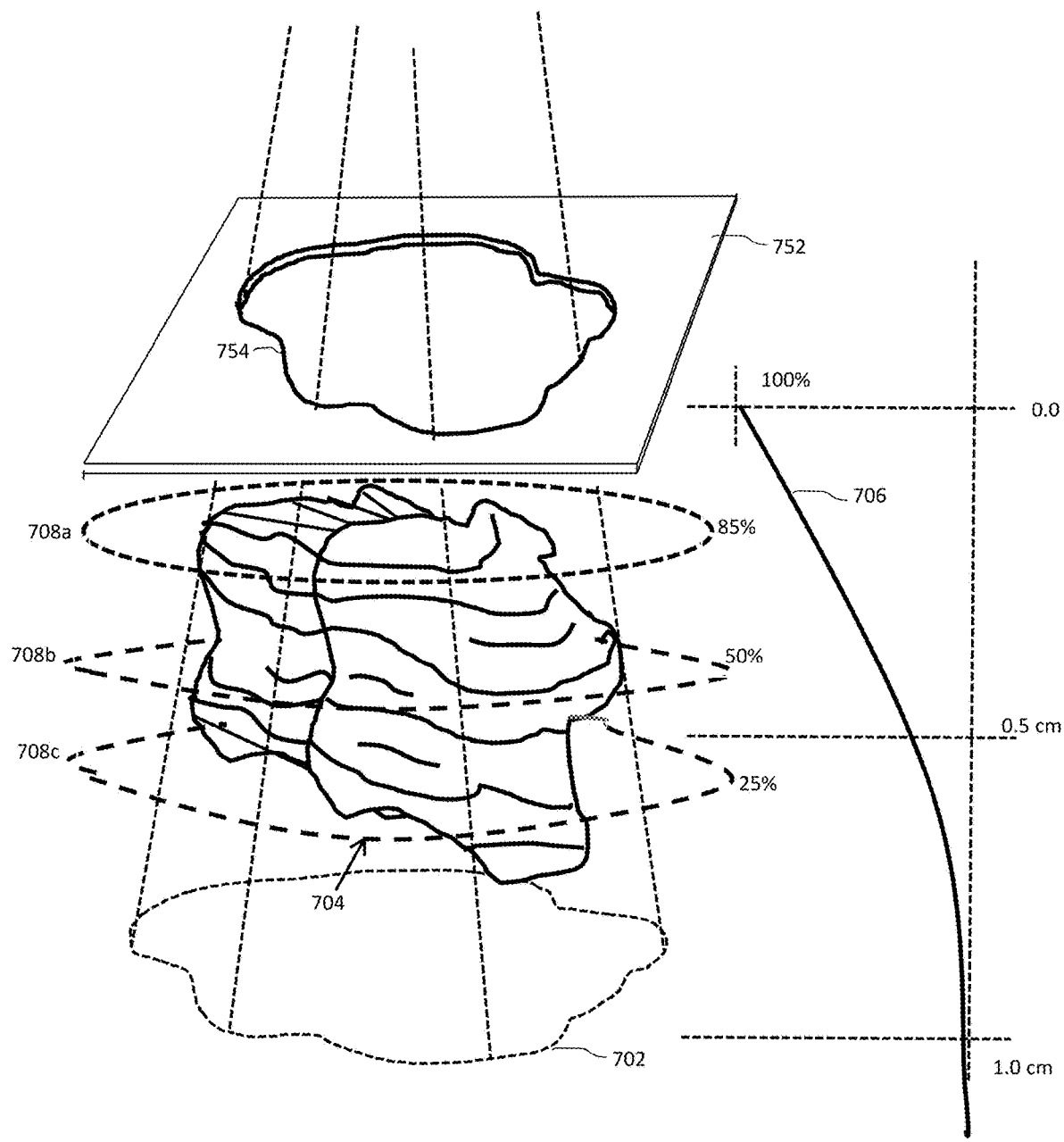
FIG. 7 is a diagram that is useful for understanding a beam projection created by using mask or shield.

Referring now to FIG. 7, a three-dimensional pattern 702 of radiation can be synthesized or modeled by a processor in an RTP system (e.g., processor 330 in RTP system 350) whereby the three-dimensional pattern is an irregularly shaped volume is determined in accordance with the captured shield image 752 and vector angle of applied radiation. Consequently, the three-dimensional pattern can visually show where radiation will be applied to underlying tissue as a result of the function of the shield and the imaged aperture 754. The irregularly shaped radiation pattern can be superimposed on a previously acquired two-dimensional or three-dimensional hybrid image of the cancerous cells 704 as described herein. The resulting composite image as shown in FIG. 7 is then presented to a treatment specialist on a display device (e.g., on base unit display device 320) of the RTP so it can be observed. The treatment specialist can then use the displayed image to visualize a resulting three-dimensional pattern of radiation which will extend through the skin tissue when using the shield 652 and applicator unit 609. The shield can then be evaluated to determine whether the resulting three-dimensional beam representation is intersecting all of the desired cancerous cells at each skin depth. Accordingly, the treatment specialist can determine whether the cancerous cells are being properly dosed with radiation in accordance with a potential treatment plan.

From the foregoing it will be understood that the three-dimensional beam pattern 702 generated by the RTP system for visualization purposes will depend in part on a beam alignment or vector direction 658 of a radiation beam applied to the tissue and screened by the shield 652. A processor associated with the RTP system (e.g. processor 330 associated with RTP system 350) can receive information about the shield aperture 654 and the radiation applicator 609 (including position and beam vector direction). Thereafter such information can be used by the RTP processor to model the beam pattern as shown in FIG. 7 and to show the extent of the three-dimensional volume of applied radiation (for visualization purposes). Such pattern can then be displayed (e.g. on a base unit display 320 or on a remote console 319) in two-dimensions or three-dimensions. Advantageously, the displayed three-dimensional image comprising the modeled radiation beam 702 can be superimposed over the hybrid image of the cancerous tissues 704 so a treatment specialist can visually evaluate whether the beam will be applied to all portions of the tissue that are determined to be cancerous.

According to a further aspect, the visualization in FIG. 7 that is obtained by using the shield 652 and vector 658 data can be combined with a further graphical display of certain data. For example, such graphical display of data can be data that is useful for understanding a radiation dose which will be applied at various tissue depths relative to a surface of the skin. The graphical data can be unique to a particular radiotherapy device 326 and associated X-ray tube 327.

As is known, a particular X-ray tube (e.g., X-ray tube 600) used for delivery of radiation therapy to a patient will have a radiation output profile which is determined by various factors. These factors can include minor variations in the manufacture of the X-ray tube and in the radiation filters 607 that are used. Accordingly, the radiation characteristic of a particular radiotherapy delivery component will generally be unique to each particular radiation therapy device or machine. For example, a Percentage Depth Dose ("PDD") plot 706 can be used to graphically show how much of a radiation dose from a particular radiation therapy machine will actually be delivered to skin tissue as a function of penetration depth. A PDD will vary in accordance with each radiotherapy system in accordance with minor variations in the X-ray tube and associated filters. Such a PDD characteristic is sometimes presented graphically. As will be appreciated, a radiation output profile such as PDD can be very important to a practitioner who needs to understand how applied radiation from the machine will interact with the tumor at various skin depths. In some embodiments, the PDD levels can be shown graphically as layers or rings 708a, 708b, 708c corresponding to the different radiation dose levels at different depths. The presentation of the PDD data in this way can allow a treatment specialist to more easily determine the amount of radiation which is to be applied to each portion of the cancerous cells 704.

Consequently, once a skin cancer has been imaged using the hybrid imaging methods described herein, it is advantageous to display the hybrid image (in two-dimensions or three-dimensions) to a treatment specialist together with a superimposed scaled graphical representation of the radiation dose profile (e.g. a PDD profile) 706 of a radiation therapy device which will actually be used to administer the radiation treatment. In this way, the treatment practitioner can visually evaluate the dose of radiation that will be delivered to various portions of the cancer as displayed, when using a particular radiation delivery device.

According to a further aspect a graphical representation of the radiation dose profile can be included in the three-dimensional representation of the radiation beam resulting from a particular shield pattern as described above. This graphic information can be combined with or overlaid on the hybrid image of the cancerous tissue as shown in FIG. 7 so that a proposed radiation treatment can be automatically evaluated by the RTP system. For example, a processor 330 associated with an RTP system 350 can evaluate whether all identified areas comprising cancerous skin cells will receive an adequate dose of radiation based on the foregoing. In some scenarios, the results of such evaluation can be communicated to a treatment specialist by highlighting or illuminating identified portions of the cancerous cells that will receive an inadequate dose of radiation. For example, such tissue areas can be highlighted in a different color to show the deficiency of the resulting three-dimensional beam pattern. All of the foregoing information can be used by the treatment specialist to develop a suitable treatment plan in accordance with step 503 in FIG. 5.

Upon completion of disease assessment 502 and therapy planning 503, the process continues at 504 where image-guided radiotherapy treatment fraction is actually delivered. A radiotherapy component or device, such as component 220 from FIG. 2 or device 326 from FIG. 3, can be used to deliver treatment according to the treatment plan. Thus, the treatment plan can be read and interpreted and X-ray beam therapy can be delivered accordingly to the designated lesion. In this regard, the X-ray beam therapy is guided by the 3D imaging and dosimetry data from the treatment plan that was specifically created for the patient and the specific skin lesion to be treated.

In one arrangement, the components of the system 250 of FIG. 2 can be used to provide the image-guided radiotherapy treatment of step 504. The treatment head 206 and treatment applicators 307, 308 can be positioned over the patient's area to be treated utilizing the built-in video-laser positioning system 215, 217. The video-laser positioning system operates to align the treated area's video image with a low opacity snapshot of the previous treatment head 206 position together with crosshairs projected by laser 217 that are projected in both real-time and previous snapshot images. The system then ensures that the treated area's video image with laser crosshairs and the low opacity snapshot with the laser crosshairs are aligned together to the exact same position, which ensures an accurate and reproducible treatment head 206 positioning over the treated lesion. Once the treatment head 206 is in place, the user engages the system 250 to deliver the treatment fraction to the lesion. The timing, energy, and geometry of the beam are all guided by the image analysis, 3D tumor modeling, and the derived physics and dosimetry calculations and analysis.

For example, treatment can be provided in multiple, short fractionated treatment sessions. Each treatment fraction or session can be less than one minute long while delivering a dose of approximately 300 cGy to approximately 500 cGy per fraction. Depending on the prescribed total dose, the lesion can be treated with one or more fractions, such as around 12 to around 30 fractions. Additional or less fractions may be used.

A treatment series can include around 5 to around 30 fractions, per the protocol the physician prescribed for a particular lesion condition. Once the lesion is defined and identified, a treatment area is defined for the circumference. This circumference, in turn, can dictate the diameter of the applicator (such as applicators 207, 208 from FIG. 2 or applicator 609 from FIG. 6) that will be used. Generally, the selected applicator for treating a particular lesion circumference can be at least 20% larger in area and/or diameter of the lesion to be treated. The clinician can create a custom lead template or shield 652 that will be cut to the size and shape of the lesion with approximately a 15% extra margin, in order to ensure that the entire malignant area will be impacted by the x-ray beam. All healthy cells that will be exposed to the x-ray beam will generally successfully recover and regenerate, while the malignant cells will go through an apoptosis from which they will not recover.

Figure 6:
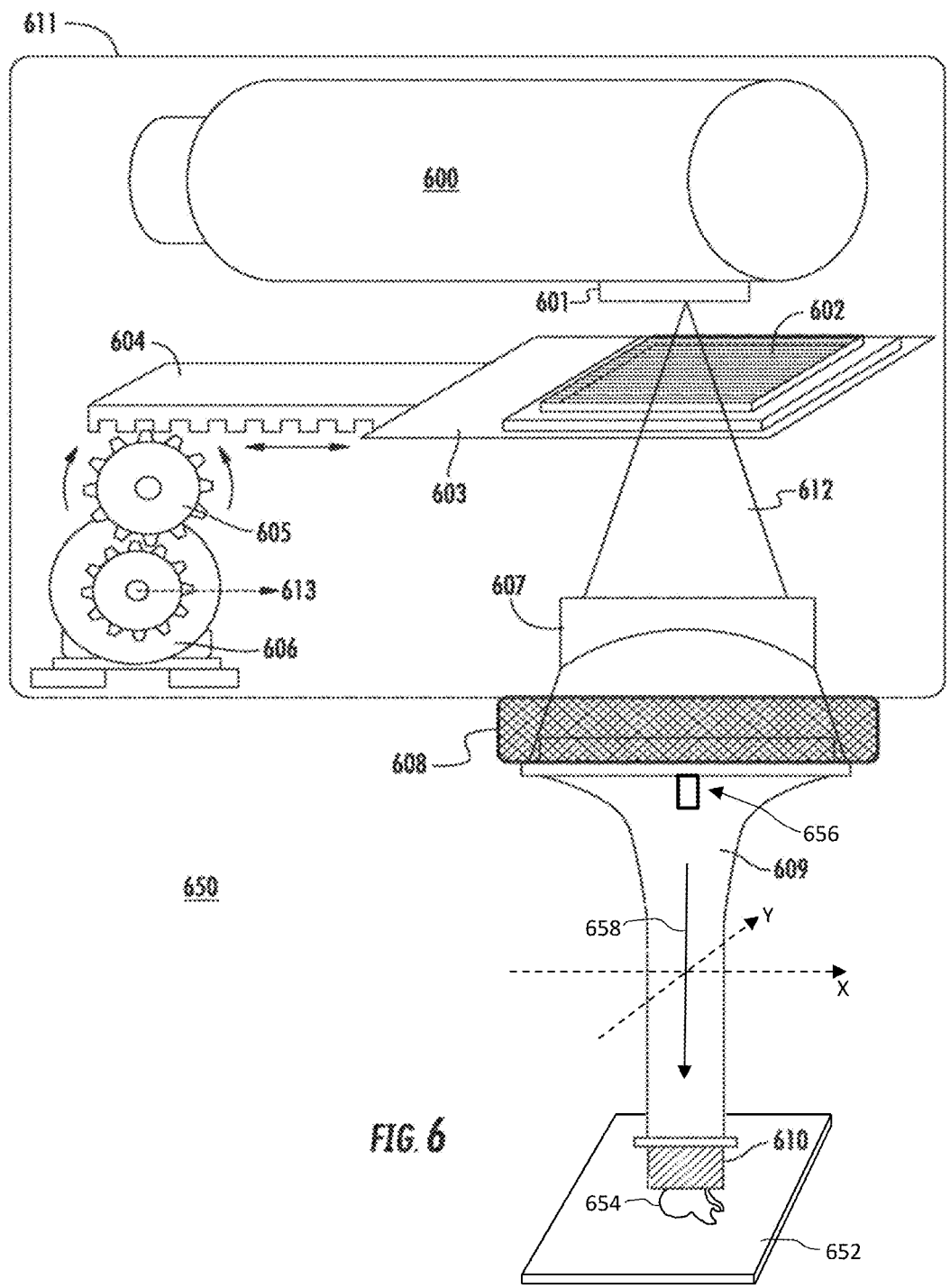
FIG. 6 is an exemplary embodiment of a beam sensing component.

As shown in FIG. 6, the template or shield 652 can be placed over the lesion, with the aperture or cutout 654 in the center of the treated area, and the selected applicator 609 will be latched onto the X-ray tube head. The treatment system can be set with the pertinent energy level and time span of the treatment (e.g., approximately 20 seconds to approximately 40 seconds), which are defined by vector tables, per the particular lesion's condition and fractionation scheme. The clinician can set the x-ray tube head vis-a-vis the applicator in position and aligned along a particular vector 658. Thereafter, the clinician can energize the system from the remote console, outside of the treatment room. The system can deliver the selected energy for the set time and can terminate treatment once the timers count to zero. The patient can be released and summoned for the next scheduled treatment session or fraction.

As will be discussed below, image-guided radiotherapy treatment step 504 can be repeated, but can be revised as needed. For instance, over the course of a treatment, a non-uniform shaped tumor may decrease in depth, width and overall size. Iterative treatments can be reduced in treatment size or intensity so that only the necessary amount of radiation is applied to as small a region as possible. In some scenarios, it can be advantageous to acquire further imaging data to characterize such changes in tumor depth, width and overall size. For example, the hybrid imaging methodology described herein can be used for this purpose. In some scenarios, additional or alternative imaging techniques can be used (such as LIDAR) to help to track the changes in the structure or anatomy of the tumor. The imaging data from these alternative methods can be combined or fused with imaging data acquired using other methods such as ultrasound and/or optical imaging methods as described.

The method 550 can then move on to the post treatment imaging phase. The post treatment imaging phase can be an iterative lesion imaging procedure that is completed after the previous imaging and assessment of the lesion. Post treatment imaging provides the ability to track and evaluate the therapy progression and healing process of the treated lesion during the fractionated therapy process. The interval of the lesion imaging is determined by the clinician according to the protocol illustrated in FIG. 8 and discussed further below.

At step 505, the treated area can again be imaged, as during the pre-treatment imaging stage. Thus, the actions and operations of step 500 can be repeated to obtain post-treatment structural and functional data for the tumor. The post treatment images and data of the treated lesion can be processed and a new fused 3D model of the tumor can be rendered in step 506. During step 506, the actions and operations of step 501 can be repeated.

The method 550 can then move to the treatment efficacy validation and analysis of steps 507 and 508, which provide for an iterative analysis of the lesion's topography and volume over time throughout the span of treatment and upon treatment completion, during the follow-up sessions. At step 507, the post treatment images and data from steps 505 and 506 can be assessed to determine how the legion responds to therapy in comparison to the anticipated healing rate, according the prescribed dosimetry and fractionation scheme of the treatment plan. Step 507 can include one or more of the actions or operations of step 502 to fully analyze a tumor or lesion.

As an example, if the newly acquired images and data indicates non-responsiveness, the treatment plan or other factors can be reviewed. In this regard, step 503 can be repeated where the treatment plan can be changed based on the post treatment imaging and assessment. On the other hand, if the newly acquired images and data indicates responsiveness, the treatment plan can be confirmed and treatment can progress. The steps provide an ongoing treated lesion assessment throughout the treatment and at its completion to evaluate the lesion evolution and its response to the therapy. The post treatment analysis can also be during the post-treatment follow-up sessions of the patient in order to document and validate or verify the full recovery and healing of the skin cancer lesion in the treated area.

Step 508, validation and confirmation of therapy efficacy and outcome can obtained. Step 508 can include image triangulation as a function of time and volume. By triangulating the 2D or 3D images, the size and shape of the tumor or lesion can be tracked. Also, volumetric analysis of the tumor over time can also be completed. The changes in the size, shape and volume of the tumor can be compared reviewed to determine effectiveness of the treatment, while factoring parameters of tumor transmutation and response to therapy. Thus, the clinician obtains an ongoing accurate assessment of the patient's response to therapy and can adjust the therapy if necessary in order to further optimize the patient's outcome. For instance, treatment session lengths or intensity can be decrease or increased. Step 508 can be completed locally by the clinician in a non-invasive manner, without any discomfort to the patient or the necessity for ancillary lab and pathology services.

At step 509, patient records can be stored and the method 550 completed. The records can include patient record data and images, results, and summary reports that illustrate the patient's disease state from procedure commencement to its ultimate conclusion. The records can be stored to local and networked record storage repositories.

Any of the steps can be repeated as needed. For instance, a tumor may require multiple treatment sessions before treatment is completed. The imaging steps, assessment and planning steps and the treatment steps may be repeated multiple times.

As all of these steps can be carried out with a single machine in a physician's office, this greatly cuts down the time, inconvenience and expense associate with diagnosis and treatment of non-melanoma skin cancer. Additionally, as it reduces or even removes the need for Mohs surgery, the patient's subsequent healing time and scarring is much reduced.

In certain configuration, the steps can be implemented via a workstation associated with the radiotherapy system. For example, computer 212, as shown in FIG. 2, can be configured with a computer program to guide the user, such as a doctor, through the various steps of FIG. 5. Thus, from computer 212, the user can perform tumor imaging and modeling processes, diagnose based on the models obtained, and plan and carry out treatment plans using the models. In other configurations, the workstation can be deployed on a remote system. For example, on another computer connected over a network to the radiotherapy system.

Turning once again to FIG. 6, a solid state beam sensor and beam sensing component 650, such as solid state beam sensor 313 and beam sensing component 312 of FIG. 3, or solid-state X-ray beam sensing component 102 of FIG. 1, can be provided. These components can be incorporated in an X-ray tube housing 611, such as the X-ray tube in treatment head 206 of FIG. 2.

The component or device 650 can include retractable support structure 603, 604 that can also be incorporated in X-ray tube housing 611. Also provided can be a x-ray imaging array detector, such as solid-state x-ray detector array 602, which is located between the X-Ray tube 600 with x-ray tube alignment 601, and a Bremsstrahlung beam-hardening aluminum filter 607. The solid-state detector array 602 that is mounted on the retractable support structure 603 can be utilized to sense the x-ray beam 612 output from the x-ray tube 600.

The retractable support structure 603 can move the solid-state detector array 602 between an X-ray testing position, as shown in FIG. 4A, and a non-testing position. In the non-testing position, the solid-state detector array 602 and/or the retractable support structure 603 is retracted or moved away from the field of emitted x-rays such that they do not absorb, block or otherwise interfere with radiation beams that are emitted from x-ray tube 600.

When the x-ray beam 612 is detected, the solid-state detector array 602 can sense characteristics of the radiation emitted from the x-ray tube 600. The detector array 602 can be used to generate a matrix-like image of the circumference of X-ray beam 612, together with the intensity of the x-ray beam's particles.

The x-ray imaging array detector can be a one-line array or a matrix array of solid state x-ray detectors that acquire and gather characteristics of the beam during the a check or testing procedure. One characteristic is the beam shape integrity, which validates that the x-ray tube output is indeed homogenous and without flaws. Another characteristic is the beam intensity that can be measured by centigray (cGy), or kilovoltage (kV) units. Other characteristics sensed by the x-ray imaging array detector include the cross section or shape of the beam. The x-ray imaging array detector can also accurately measure the photons emitted from the x-ray tube 600. Further, the x-ray imaging array detector can also be used to determine whether the x-ray tube port 601 is properly aligned or if realignment is needed.

The collected data can be communicated to the beam sensing component, such as beam sensing component 312 of FIG. 3 that pre-processes the data. The pre-processed data can be communicated with a processor, such as processor 330, for further analysis and visualization. The solid state beam sensor and beam sensing component can be utilized as a daily quality control tool and for overall system diagnosis purposes. For instance, the solid state beam sensor and beam sensing component may detect a difference between the programmed radiation and what is output from the X-ray tube 600. Detection can allow for maintenance to ensure desired treatment dosages are delivered. Still further, testing can be automated before use such that the emitted x-rays and/or alignment of the x-ray tube port 601 is confirmed prior to each use.

The retractable support structure 603, 604 can include at least one motor or actuator 613 and positioning components 605, 606. The motor or actuator 613 can be controlled via a processor, such as processor 330 with the beam sensing component 314. The motor or actuator 613 can move the solid-state detector array 602 between the X-ray testing position and the non-testing position.

FIG. 6 also shows a removable treatment head or applicator 609 with tip 610 that can be changed to suit the treatment area and depth needed. Suitable treatment heads that may be used in the component 650 can include treatment applicators, ranging from approximately 1 cm through approximately 7.3 cm diameter heads at approximately 15 cm SSD, and also approximately 1 cm through approximately 12.7 cm diameter heads at approximately 25 cm SSD. The removable head 609 can be used with radiotherapy devices 220 and 326.

Figure 8:
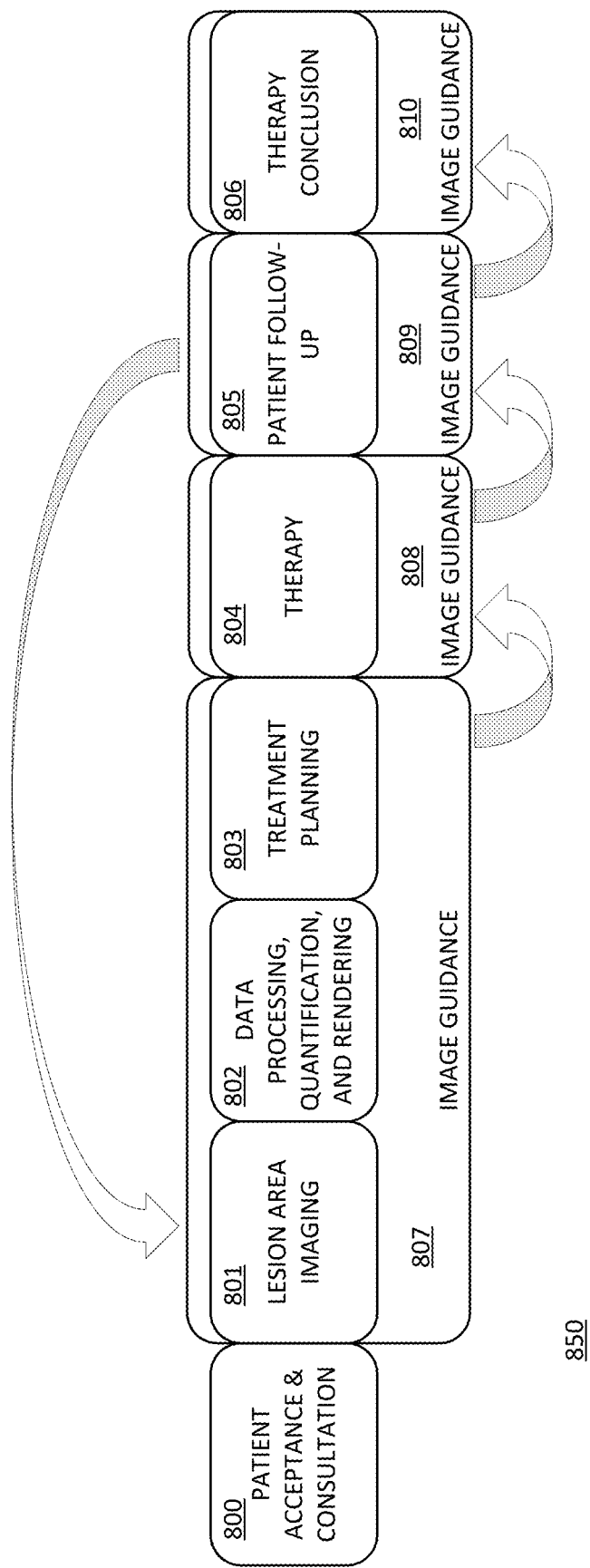
FIG. 8 is a flow diagram of a process of treating a patient.

FIG. 8 provides a flow chart of patient and treatment management protocol 850. When a patient first arrives at a doctor or clinician, the patient acceptance and consultation step 800 can occur. In this step, the patient is registered in the practice's workflow management system that can be integrated with a hybrid image-guided superficial radiotherapy system that can employ protocols such as DICOM and HL7, such as the system 350 illustrated at FIG. 3 or any suitable system.

With registration, the patient can be scheduled for the initial prognosis and consultation with the clinician. During initial prognosis and consultation, the patient can be scanned by an imaging device at 801 to obtain structural and functional information, as part of the image guidance phase 807. The scanning provides the clinician and the patient an assessment of any lesions and the disease state before making a decision on the recommended and preferred treatment path. The scanned lesion image data is then processed and reconstructed at step 802 to render the 2D image slices of the scanned area that contain the 2D cross-sections of the tumor. If desired, these images can be reviewed. The 2D tumor data can also converted to a 3D volumetric model and rendered to derive all the volumetric and physiological data of the tumor out of the scanned lesion, all for use in the next step.

Treatment planning step 803, uses the quantified data to calculate and generate a personalized treatment plan for the patient and the treated lesion.

Therapy can then commence at step 804, while imaging is still being applied 808 in varying intervals according to the clinician's and treatment plan's protocol to monitor and guide the course of the therapy throughout the prescribed fractions and entire treatment span.

Patient follow-up sessions 805 can be conducted to verify and monitor the full recovery of the treated lesion. As an example, follow-up sessions can be completed months or years after the last therapy session to monitor the area of a treated lesion. This stage is also being image-guided 809 with images obtained with a high frequency ultrasound device in order to add further validity to the treatment's outcome and to verify that indeed the lesion is completely cured and gone.

When the entire therapy sequence is complete at step 806, the patient data and all pertinent image-guidance data 810 is archived and submitted to the medical record management systems and the healthcare management systems. By generally the entire treatment process including non-invasive imaging as a substitute to invasive, time consuming, and expensive biopsies, the patient management protocol is being dramatically enhanced and improved, which offers benefits to all entities and parties involved, including the patient, the clinician, and the healthcare system as a whole.

The systems, methods and devices include broader applications beyond treating lesions or skin cancer. For instance, the systems, methods and devices can be utilized as intra operative radiotherapy in surgical environments to treat other cancers or lesions when their respective tumors are surgically removed. In addition to removal of a tumor, an excised area can imaged, analyzed and treated with the systems, methods and devices herein, such as treating an excised area with one or more 21 Gy fractions before the patient is sutured.

In some arrangements, the systems, devices, methods and protocols can be employed for relatively superficial tumors that are not skin cancers, such as certain breast cancers, in which case the treatment head can include a surgical catheter for insertion beneath the skin, together with a small scale spherical treatment head.

It is important to note that the methods described above may incorporate any of the functionality, devices, and/or features of the systems described above, or otherwise, and are not intended to be limited to the description or examples provided herein.

Referring now also to FIG. 9, at least a portion of the methodologies and techniques described with respect to the exemplary embodiments can incorporate a machine, such as, but not limited to, computer system 900, or other computing device within which a set of instructions, when executed, may cause the machine to perform any one or more of the methodologies or functions discussed above. The machine may be configured to facilitate various operations conducted by the systems illustrated at FIGS. 3 and 4. For example, the machine may be configured to, but is not limited to, assist these systems by providing processing power to assist with processing loads experienced in the systems, by providing storage capacity for storing instructions or data traversing the systems, or by assisting with any other operations conducted by or within the systems.

In some embodiments, the machine operates as a stand-alone device. In some embodiments, the machine may be connected (e.g., using a network 935) via a network interface, such as network interface 328, to and assist with operations performed by other machines, such as, but not limited to, the radiotherapy device 326, central diagnostics component 312, the data repositories 304 and 305, the SRT control component 308 or the other devices and components of the system at FIG. 3, including any combination thereof. The machine may be connected with any component in the system at FIG. 3. In a networked deployment, the machine may operate in the capacity of a server or a client user machine in server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 900 may include a processor 902 (e.g., a central processing unit (CPU), a graphics processing unit (GPU, or both), a main memory 904 and a static memory 906, which communicate with each other via a bus 908. The computer system 900 may further include a video display unit 910 (e.g., a liquid crystal display (LCD), a flat panel, a solid state display, or a cathode ray tube (CRT)). The computer system 900 may include an input device 912 (e.g., a keyboard), a cursor control device 914 (e.g., a mouse), a disk drive unit 916, a signal generation device 918 (e.g., a speaker or remote control) and a network interface device 920.

The disk drive unit 916 may include a machine-readable medium 922 on which is stored one or more sets of instructions 924 (e.g., software) embodying any one or more of the methodologies or functions described herein, including those methods illustrated above. The instructions 924 may also reside, completely or at least partially, within the main memory 904, the static memory 906, or within the processor 902, or a combination thereof, during execution thereof by the computer system 900. The main memory 904 and the processor 902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium 922 containing instructions 924 so that a device connected to the communications network 935 can send or receive voice, video or data, and to communicate over the network 935 using the instructions. The instructions 924 may further be transmitted or received over the network 935 via the network interface device 920.

While the machine-readable medium 922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. In one embodiment, the machine readable storage medium may be a machine readable storage device or a computer readable device. Accordingly, the disclosure is considered to include any one or more of a machine-readable medium or a distribution medium, as listed herein and including art-recognized equivalents and successor media, in which the software implementations herein are stored.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A radiotherapy method for treatment of skin, comprising:
    acquiring structural imaging data for a region of interest in the skin of a patient using high frequency ultrasound;
    acquiring functional imaging data for the region of interest using optical imaging;
    combining the structural imaging data and the functional imaging data to produce a fused model for a least a portion of the region of interest;
    generating a plan for radiotherapy treatment of the region of interest based on the fused model; and
    applying the radiotherapy treatment according to the plan.

2. The method of claim 1, wherein acquiring the structural imaging data comprises obtaining a plurality of two-dimensional (2D) images of the region of interest using high frequency ultrasound.

3. The method of claim 2, wherein the plurality of 2D images comprise at least two 2D images that represent two slices of the region of interest that are perpendicular to each other.

4. The method of claim 1, wherein acquiring the functional imaging data comprises using optical imaging of the region of interest in conjunction with the use of at least one biomarker substance.

5. The method of claim 1, wherein generating the radiotherapy treatment plan comprises using the fused model to identify a treatment volume in the patient to which radiation is to be applied, and selecting one or more radiotherapy parameters based at least on the treatment volume.

6. The method according to claim 5, wherein the radiation is selected to comprise a low energy X-ray radiation for superficial radiation therapy (SRT).

7. The method of claim 5, wherein generating the radiotherapy treatment plan further comprises determining one or more portions of the fused model requiring radiotherapy treatment, and wherein the radiotherapy parameters are further based on the one or more portions.

8. The method of claim 5, further comprising automatically generating a data file specifying a pattern for a radiation attenuating mask, wherein the pattern is based on the fused model.

9. The method according to claim 8, further comprising outputting the data file to an automated fabrication machine capable of producing the mask based on the data file.

10. The method of claim 1, wherein the radiotherapy treatment comprises at least one of photon-based radiotherapy or particle-based radiotherapy.

11. A radiotherapy system for radiotherapy planning and treatment of skin, comprising:
    a radiotherapy component comprising a radiation source configured for superficial radiation therapy (SRT);
    a structural imaging component which comprises a high frequency ultrasound source to differentiate among a plurality of tissue types in human skin;
    a functional imaging component comprising an optical imager configured to capture one or more optical images of human skin; and
    a workstation coupled to the radiotherapy component, the structural imaging component, and the functional imaging component, the workstation comprising a processor and a computer-readable medium having stored thereon instruction for causing the processor to:
        acquire, by using the structural imaging component, structural imaging data for a region of interest comprising a superficial portion of a patient's skin;
        acquire, by using the functional imaging component, functional imaging data for the region of interest;
        combine the structural imaging data and the functional imaging data to produce a fused model for a least a portion of the region of interest;
        generate a plan for radiotherapy treatment of the region of interest based on the fused model; and
        control the radiotherapy component, for carrying out the radiotherapy treatment according to the plan.

12. The system of claim 11, wherein the structural imaging component comprises a high frequency ultrasound component which generates a plurality of two-dimensional (2D) images of the region of interest using high frequency ultrasound.

13. The system of claim 12, wherein the function imaging data comprises at least two 2D images that represent two slices of the region of interest that are perpendicular to each other.

14. The system of claim 11, wherein the functional imaging component is responsive to photonic emissions from at least one biomarker to identify functional data associated with tissue.

15. The system of claim 11, wherein generating the radiotherapy treatment plan comprises using the fused model to identify a treatment volume in the patient to which radiation is to be applied, and selecting one or more radiotherapy parameters for operating the radiotherapy component based at least on the treatment volume.

16. The system of claim 15, wherein generating the radiotherapy treatment plan further comprises determining one or more portions of the fused model requiring radiotherapy treatment, and wherein the radiotherapy parameters are further based on the one or more portions.

17. The system of claim 11, wherein the radiotherapy treatment comprises at least one of photon-based radiotherapy or particle-based radiotherapy.

18. The system according to claim 11, wherein the computer-readable medium has stored thereon instruction for causing the processor to generate a data file specifying a pattern for a radiation attenuating mask.

19. The system according to claim 18, wherein the computer-readable medium has stored thereon instruction for causing the processor to output the data file to an automated fabrication machine capable of producing the mask based on the data file.

* * * * *